United States Patent [19]
Conklin et al.

[11] Patent Number: 6,046,028
[45] Date of Patent: Apr. 4, 2000

[54] POLYNUCLEOTIDES ENCODING INSULIN HOMOLOG ZINS3

[75] Inventors: Darrell C. Conklin, Seattle; Catherine E. Lofton-Day, Brier; Si Lok, Seattle; Stephen R. Jaspers, Edmonds, all of Wash.

[73] Assignee: ZymoGenetics, Inc., Seattle, Wash.

[21] Appl. No.: 08/950,720

[22] Filed: Oct. 15, 1997

Related U.S. Application Data

[60] Provisional application No. 60/028,177, Oct. 15, 1996.

[51] Int. Cl.[7] .......................... C12N 15/17; C12N 15/63; C12N 5/10; C07K 14/62
[52] U.S. Cl. ........................ 435/69.1; 435/69.1; 435/69.4; 435/325; 435/320.1; 536/23.1; 536/23.51; 536/24.3; 530/350
[58] Field of Search .................................. 435/69.1, 69.4, 435/325, 243, 320.1; 536/23.1, 23.51, 24.3; 530/350

[56] References Cited

PUBLICATIONS

LIFESEQ™ Clone Information Results, Incyte Pharmaceuticals Inc., 1996.
Sakbun et al., *Journal of Clinical Endocrinology and Metabolism* 70: 508–514, 1990.
Yamamoto et al., *Journal of Clinical Endocrinology and Metabolism* 52: 601–604, 1981.

*Primary Examiner*—Prema Mertz
*Assistant Examiner*—Fozia Hamud
*Attorney, Agent, or Firm*—Deborah A. Sawislak

[57] ABSTRACT

The present invention relates to polynucleotides encoding for novel insulin homolog polypeptides that have been designated Zins3. The human and mouse polynucleotides and corresponding polypeptides are described, and comprise a B chain, A chain, and C-peptide, or portions thereof. The polynucleotide sequence maps to human chromosome 12.

10 Claims, 2 Drawing Sheets

```
IGF1_HUMAN    MSSSHLFYLALCLLTFTSSATA------------GPETLCGAELVDALQFVCGDRGF; 45
IGF2_HUMAN    MGIPMGKSMLVLLTFLAFASCCIA-------AYRPSETLCGGELVDTLQFVCGDRGF; 50
INS_HUMAN     MALWMRLLPLLALLALWGPDPAAA---------FVNQHLCGSHLVEALYLVCGERGF; 48
REL2_HUMAN    MPRLFFFHLLGVCLLLNQFSRAVA-----DSWMEEVIKLCGRELVRAQIAICGMSTW; 52
REL1_HUMAN    MPRLFLFHLLEFCLLLNQFSRAVAA-----KWKDDVIKLCGRELVRAQIAICGMSTW; 52
INL3_HUMAN    MDPRLPAWALVLLGPALVFA------LGPAPTPEMREKLCGHHFVRALVRVCGGPRW; 51
INSL4         MASLFRSYLPAIWLLLSQLLRESLA---------AELRGCGPRFGKHLLSYCPMPEK; 48
zins3_human   MKGSIFTLFLFSVLFAISEVRS------------KESVRLCGLEYIRTVIYICASSRW; 46
mzins3        MKGPTLALFLLLVLLAVVEVRS------------RQTVKLCGLDYRRTVIYICASSRW; 46
Consensus:    M         l !!l !                    $lCG  v  !  !Cg    #
Identity:     *                                     **         *

IGF1_HUMAN    YFN--------------KPTGYGSSSRRAPQT------------------------; 63
IGF2_HUMAN    YFSRPA-----------------SRVSRRSR-------------------------; 64
INS_HUMAN     FYTPKTRR--------EAEDLQVGQVELGGGPGAGSLQPLALEGSLQKR--------; 89
REL2_HUMAN    SKR-------------SLSQEDAPQTPRPVAEIVPSFINKDTETINMMSEFVANLPQ; 96
REL1_HUMAN    SKR-------------SLSQEDAPQTPRPVAEIVPSFINKDTETIIIMLEFIANLPP; 96
INL3_HUMAN    STEARR----------PAAGGDLPQTSHHHRHHR----------------------; 75
INSL4         TFTTTPGGWL----LESGRPKEMVSTSNNKDGQALGTTSEFIPNLSPELKKPLSEGQ; 101
zins3_human   RR----------HLEGIPQAQQAETGNSFQLPHKREFSEENPAQNLPKVDASGEDR; 92
mzins3        RR----------HLEGHFHSQQAETRNYLQLLDRHEPSKKTLEHSLPKTDLSGQEL; 92

IGF1_HUMAN    --------------------------------------------------------; 63
IGF2_HUMAN    --------------------------------------------------------; 64
INS_HUMAN     --------------------------------------------------------; 89
REL2_HUMAN    ELKLTLSEMQPALPQLQQHVPVLKDSSLLFEEFKKLIRNRQSEAADSSPSELKYLGL; 153
REL1_HUMAN    ELKAALSERQPSLPELQQYVPALKDSNLSFEEFKKLIRNRQSEAADSNPSELKYLGL; 153
INL3_HUMAN    --------------------------------------------------------; 75
INSL4         PSLKKIILSRKKR-------------------------------------------; 114
zins3_human   LWGGQMPTEELWKSKKHSVMSR----------------------------------; 114
mzins3        VRDPQAPKEGLWELKKHSVVSRR---------------------------------; 115

IGF1_HUMAN    ---------------------GIVDECCFRSCDLRRLEMYCAPLKPAKSARSVRA; 97
IGF2_HUMAN    ---------------------GIVEECCFRSCDLALLETYCATPAKSERDVSTPP; 98
INS_HUMAN     ---------------------GIVEQCCTSICSLYQLENYCN            ; 110
REL2_HUMAN    DTHSRKKR----------QLYSALANKCCHVGCTKRSLARFC             ; 185
REL1_HUMAN    DTHSQKKR----------RPYVALFEKCCLIGCTKRSLAKYC             ; 185
INL3_HUMAN    ---------------AAATNPARYCCLSGCTQQDLLTLCPY              ; 101
INSL4         ---------------SGRHRFDPFCCEVICDDGTSVKLCT               ; 139
zins3_human   -----------------------QDLQTLCCTDGCSMTDLSALC           ; 135
mzins3        ------------------------DLQALCCREGCSMKELSTLC           ; 135
Consensus:                                CC !C%    l     C
Identity:                                 **    *      *

IGF1_HUMAN    QRHTDMPKTQKEVHLKNASRGSAGNKNYRM                         ; 127
IGF2_HUMAN    TVLPDNFPRYPVGKFFQYDTWKQSTQRLRRGLPALLRARRGHVLAKELEAFREAKRH; 155
Consensus:                                  R
Identity:                                   *

IGF1_HUMAN    RPLIALPTQDPAHGGAPPEMASNRK                              ; 180
```

FIG. 1

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 792 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: Coding Sequence
      (B) LOCATION: 77...481
      (D) OTHER INFORMATION:

(xi) SEQUENCE DESCRIPTION: SEQ ID NO:1:

```
GTCGACCCAC GCGTCCGCGG ACGCGTGGGC GGACGCGTGG GTTACCATAT CAGATTCACA        60

TTCAGTCCTC AGCAAA ATG AAG GGC TCC ATT TTC ACT CTG TTT TTA TTC TCT       112
               Met Lys Gly Ser Ile Phe Thr Leu Phe Leu Phe Ser
                 1               5                  10

GTC CTA TTT GCC ATC TCA GAA GTG CGG AGC AAG GAG TCT GTG AGA CTC         160
Val Leu Phe Ala Ile Ser Glu Val Arg Ser Lys Glu Ser Val Arg Leu
         15                  20                  25

TGT GGG CTA GAA TAC ATA CGG ACA GTC ATC TAT ATC TGT GCT AGC TCC         208
Cys Gly Leu Glu Tyr Ile Arg Thr Val Ile Tyr Ile Cys Ala Ser Ser
     30                  35                  40

AGG TGG AGA AGG CAT CTG GAG GGG ATC CCT CAA GCT CAG CAA GCT GAG         256
Arg Trp Arg Arg His Leu Glu Gly Ile Pro Gln Ala Gln Gln Ala Glu
 45                  50                  55                  60

ACA GGA AAC TCC TTC CAG CTC CCA CAT AAA CGT GAG TTT TCT GAG GAA         304
Thr Gly Asn Ser Phe Gln Leu Pro His Lys Arg Glu Phe Ser Glu Glu
                 65                  70                  75

AAT CCA GCG CAA AAC CTT CCG AAG GTG GAT GCC TCA GGG GAA GAC CGT         352
Asn Pro Ala Gln Asn Leu Pro Lys Val Asp Ala Ser Gly Glu Asp Arg
             80                  85                  90

CTT TGG GGT GGA CAG ATG CCC ACT GAA GAG CTT TGG AAG TCA AAG AAG         400
Leu Trp Gly Gly Gln Met Pro Thr Glu Glu Leu Trp Lys Ser Lys Lys
         95                 100                 105

CAT TCA GTG ATG TCA AGA CAA GAT TTA CAA ACT TTG TGT TGC ACT GAT         448
His Ser Val Met Ser Arg Gln Asp Leu Gln Thr Leu Cys Cys Thr Asp
     110                 115                 120

GGC TGT TCC ATG ACT GAT TTG AGT GCT CTT TGC TAAGACAAGA GCAAATACCC       501
Gly Cys Ser Met Thr Asp Leu Ser Ala Leu Cys
125                 130                 135

AATGGGTGGC AGAGCTTTAT CACATGTTTA ATTACAGTGT TTTACTGCCT GGTAGAACAC       561
```

```
TAATATTGTG TTATTAAAAT GATGGCTTTT GGGTAGGCAA AACTTCTTTT CTAAAGGTAT      621

AGCTGAGCGG TTGAAACCAC AGTGATCTCT ATTTTCTCCC TTTGCCAAGG TTAATGAACT      681

GTTCTTTTCA AATTCTACTA ATGCTTTGAA ATTTCAAATG CTGCGCAAAA TTGCAATAAA      741

AATGCTATAA ACCAAAAAAA AAAAAAAAAG GGCGGCCGCT CTAGAGGATC C              792
```

(2) INFORMATION FOR SEQ ID NO:2:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Lys Gly Ser Ile Phe Thr Leu Phe Leu Phe Ser Val Leu Phe Ala
 1               5                  10                  15

Ile Ser Glu Val Arg Ser Lys Glu Ser Val Arg Leu Cys Gly Leu Glu
             20                  25                  30

Tyr Ile Arg Thr Val Ile Tyr Ile Cys Ala Ser Ser Arg Trp Arg Arg
         35                  40                  45

His Leu Glu Gly Ile Pro Gln Ala Gln Gln Ala Glu Thr Gly Asn Ser
     50                  55                  60

Phe Gln Leu Pro His Lys Arg Glu Phe Ser Glu Asn Pro Ala Gln
 65                  70                  75                  80

Asn Leu Pro Lys Val Asp Ala Ser Gly Glu Asp Arg Leu Trp Gly Gly
                 85                  90                  95

Gln Met Pro Thr Glu Glu Leu Trp Lys Ser Lys Lys His Ser Val Met
            100                 105                 110

Ser Arg Gln Asp Leu Gln Thr Leu Cys Cys Thr Asp Gly Cys Ser Met
        115                 120                 125

Thr Asp Leu Ser Ala Leu Cys
    130                 135
```

(2) INFORMATION FOR SEQ ID NO:3:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (vii) IMMEDIATE SOURCE:
        (B) CLONE: ZC11142

(xi) SEQUENCE DESCRIPTION: SEQ ID NO:3:

```
CAGGTGGAGA AGGCATCTG                                                   19
```

(2) INFORMATION FOR SEQ ID NO:4:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (vii) IMMEDIATE SOURCE:
        (B) CLONE: ZC11140

(xi) SEQUENCE DESCRIPTION: SEQ ID NO:4:

```
GGTATTTGCT CTTGTCTTAG C                                                               21

(2) INFORMATION FOR SEQ ID NO:5:

(i) SEQUENCE CHARACTERISTICS:
        (A) LENGTH: 735 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 52...456
        (D) OTHER INFORMATION:

(xi) SEQUENCE DESCRIPTION: SEQ ID NO:5:

GAATTCGTCG ACATGGCTGA CCACATTGCT TCTCATTTGC TCTCCGGCAG G ATG AAG        57
                                                         Met Lys
                                                           1

GGC CCC ACT CTT GCT CTG TTT CTC CTC TTA GTT CTG TTG GCT GTG GTG       105
Gly Pro Thr Leu Ala Leu Phe Leu Leu Leu Val Leu Leu Ala Val Val
         5                  10                  15

GAA GTA AGA AGC AGG CAG ACT GTG AAG CTC TGT GGC CTG GAC TAC GTG       153
Glu Val Arg Ser Arg Gln Thr Val Lys Leu Cys Gly Leu Asp Tyr Val
 20                  25                  30

AGA ACA GTT ATC TAC ATC TGT GCC AGC TCA CGG TGG AGA AGA CAT CTG       201
Arg Thr Val Ile Tyr Ile Cys Ala Ser Ser Arg Trp Arg Arg His Leu
 35                  40                  45                  50

GAG GGG CAT TTC CAC TCT CAA CAA GCT GAG ACA AGA AAC TAC CTC CAG       249
Glu Gly His Phe His Ser Gln Gln Ala Glu Thr Arg Asn Tyr Leu Gln
                     55                  60                  65

CTC CTA GAC AGG CAC GAG CCA TCC AAG AAA ACT CTG GAG CAC AGC CTT       297
Leu Leu Asp Arg His Glu Pro Ser Lys Lys Thr Leu Glu His Ser Leu
             70                  75                  80

CCC AAG ACG GAT CTC TCA GGA CAG GAG CTT GTT CGA GAT CCA CAG GCA       345
Pro Lys Thr Asp Leu Ser Gly Gln Glu Leu Val Arg Asp Pro Gln Ala
         85                  90                  95

CCC AAG GAA GGT CTT TGG GAA CTG AAG AAG CAC TCA GTG GTA TCC AGA       393
Pro Lys Glu Gly Leu Trp Glu Leu Lys Lys His Ser Val Val Ser Arg
100                 105                 110

CGA GAT CTG CAA GCT CTG TGC TGC AGG GAA GGC TGC TCC ATG AAG GAA       441
Arg Asp Leu Gln Ala Leu Cys Cys Arg Glu Gly Cys Ser Met Lys Glu
115                 120                 125                 130

CTC AGC ACC CTC TGT TAGGATGCGC CCAACCCCTT GGCAGGCTTC AGCATGCATC T     497
Leu Ser Thr Leu Cys
                135

CAATGTTCTA CCATCGAGTT CCCTGTTCAG CTTCTATCAC TACAACCACG GCTTTTGATC     557

CTTTCCTTAA AGGTCTATTA TGGCTTAAAG CCACTCTTCT CCCTGTGCTG AGGTCAATCT     617

ACTTTTCTTT CTAAATTCTA ACTACTGCTT TGAAGTTTCA AGTGCTGTGC AAAATTGCAA     677

TAAAAAAAAA TGCCTGAATC CAAAAAAAAA AAAAAAAAA AAAAAAAGG GCGGCCGC        735

(2) INFORMATION FOR SEQ ID NO:6:

(i) SEQUENCE CHARACTERISTICS:
        (A) LENGTH: 135 amino acids
        (B) TYPE: amino acid
        (C) STRANDEDNESS: single
        (D) TOPOLOGY: linear (ii) MOLECULE TYPE: protein (v) FRAGMENT TYPE: internal
```

(xi) SEQUENCE DESCRIPTION: SEQ ID NO:6:

```
Met Lys Gly Pro Thr Leu Ala Leu Phe Leu Leu Val Leu Leu Ala
 1               5                  10                  15

Val Val Glu Val Arg Ser Arg Gln Thr Val Lys Leu Cys Gly Leu Asp
            20                  25                  30

Tyr Val Arg Thr Val Ile Tyr Ile Cys Ala Ser Ser Arg Trp Arg Arg
                35                  40                  45

His Leu Glu Gly His Phe His Ser Gln Gln Ala Glu Thr Arg Asn Tyr
    50                  55                  60

Leu Gln Leu Leu Asp Arg His Glu Pro Ser Lys Lys Thr Leu Glu His
65                  70                  75                  80

Ser Leu Pro Lys Thr Asp Leu Ser Gly Gln Glu Leu Val Arg Asp Pro
                85                  90                  95

Gln Ala Pro Lys Glu Gly Leu Trp Glu Leu Lys Lys His Ser Val Val
                100                 105                 110

Ser Arg Arg Asp Leu Gln Ala Leu Cys Cys Arg Glu Gly Cys Ser Met
            115                 120                 125

Lys Glu Leu Ser Thr Leu Cys
            130                 135
```

(2) INFORMATION FOR SEQ ID NO:7:

(i) SEQUENCE CHARACTERISTICS:
        (A) LENGTH: 405 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ATGAARGGNW SNATHTTYAC NYTNTTYYTN TTYWSNGTNY TNTTYGCNAT HWSNGARGTN      60

MGNWSNAARG ARWSNGTNMG NYTNTGYGGN YTNGARTAYA THMGNACNGT NATHTAYATH     120

TGYGCNWSNW SNMGNTGGMG NMGNCAYYTN GARGGNATHC CNCARGCNCA RCARGCNGAR    180

ACNGGNAAYW SNTTYCARYT NCCNCAYAAR MGNGARTTYW SNGARGARAA YCCNGCNCAR    240

AAYYTNCCNA ARGTNGAYGC NWSNGGNGAR GAYMGNYTNT GGGGNGGNCA RATGCCNACN    300

GARGARYTNT GGAARWSNAA RAARCAYWSN GTNATGWSNM GNCARGAYYT NCARACNYTN    360

TGYTGYACNG AYGGNTGYWS NATGACNGAY YTNWSNGCNY TNTGY                    405
```

(2) INFORMATION FOR SEQ ID NO:8:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp Tyr Lys Asp Asp Asp Asp Lys
 1               5
```

(2) INFORMATION FOR SEQ ID NO:9:

(i) SEQUENCE CHARACTERISTICS:
        (A) LENGTH: 152 amino acids
        (B) TYPE: amino acid (C) STRANDEDNESS: single
(D) TOPOLOGY: linear (ii) MOLECULE TYPE: None (xi) SEQUENCE DESCRIPTION: SEQ ID NO:9:

```
Met Ser Ser Ser His Leu Phe Tyr Leu Ala Leu Cys Leu Leu Thr Phe
1               5                   10                  15

Thr Ser Ser Ala Thr Ala Gly Pro Glu Thr Leu Cys Gly Ala Glu Leu
            20                  25                  30

Val Asp Ala Leu Gln Phe Val Cys Gly Asp Arg Gly Phe Tyr Phe Asn
            35                  40                  45

Lys Pro Thr Gly Tyr Gly Ser Ser Arg Arg Ala Pro Gln Thr Gly
        50                  55                  60

Ile Val Asp Glu Cys Cys Phe Arg Ser Cys Asp Leu Arg Arg Leu Glu
65                  70                  75                  80

Met Tyr Cys Ala Pro Leu Lys Pro Ala Lys Ser Ala Arg Ser Val Arg
                85                  90                  95

Ala Gln Arg His Thr Asp Met Pro Lys Thr Gln Lys Glu Val His Leu
            100                 105                 110

Lys Asn Ala Ser Arg Gly Ser Ala Gly Asn Lys Asn Tyr Arg Met Arg
        115                 120                 125

Pro Leu Ile Ala Leu Pro Thr Gln Asp Pro Ala His Gly Gly Ala Pro
    130                 135                 140

Pro Glu Met Ala Ser Asn Arg Lys
145                 150
```

(2) INFORMATION FOR SEQ ID NO:10:

(i) SEQUENCE CHARACTERISTICS:
        (A) LENGTH: 155 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:10:

```
Met Gly Ile Pro Met Gly Lys Ser Met Leu Val Leu Leu Thr Phe Leu
1               5                   10                  15

Ala Phe Ala Ser Cys Cys Ile Ala Ala Tyr Arg Pro Ser Glu Thr Leu
            20                  25                  30

Cys Gly Gly Glu Leu Val Asp Thr Leu Gln Phe Val Cys Gly Asp Arg
            35                  40                  45

Gly Phe Tyr Phe Ser Arg Pro Ala Ser Arg Val Ser Arg Arg Ser Arg
        50                  55                  60

Gly Ile Val Glu Glu Cys Cys Phe Arg Ser Cys Asp Leu Ala Leu Leu
65                  70                  75                  80

Glu Thr Tyr Cys Ala Thr Pro Ala Lys Ser Glu Arg Asp Val Ser Thr
                85                  90                  95

Pro Pro Thr Val Leu Pro Asp Asn Phe Pro Arg Tyr Pro Val Gly Lys
            100                 105                 110

Phe Phe Gln Tyr Asp Thr Trp Lys Gln Ser Thr Gln Arg Leu Arg Arg
        115                 120                 125

Gly Leu Pro Ala Leu Leu Arg Ala Arg Arg Gly His Val Leu Ala Lys
    130                 135                 140

Glu Leu Glu Ala Phe Arg Glu Ala Lys Arg His
145                 150                 155
```

(2) INFORMATION FOR SEQ ID NO:11:

(i) SEQUENCE CHARACTERISTICS:
        (A) LENGTH: 110 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:11:

```
Met Ala Leu Trp Met Arg Leu Leu Pro Leu Leu Ala Leu Leu Ala Leu
 1               5                  10                  15

Trp Gly Pro Asp Pro Ala Ala Ala Phe Val Asn Gln His Leu Cys Gly
            20                  25                  30

Ser His Leu Val Glu Ala Leu Tyr Leu Val Cys Gly Glu Arg Gly Phe
        35                  40                  45

Phe Tyr Thr Pro Lys Thr Arg Arg Glu Ala Glu Asp Leu Gln Val Gly
 50                  55                  60

Gln Val Glu Leu Gly Gly Gly Pro Gly Ala Gly Ser Leu Gln Pro Leu
65                  70                  75                  80

Ala Leu Glu Gly Ser Leu Gln Lys Arg Gly Ile Val Glu Gln Cys Cys
                85                  90                  95

Thr Ser Ile Cys Ser Leu Tyr Gln Leu Glu Asn Tyr Cys Asn
            100                 105                 110
```

(2) INFORMATION FOR SEQ ID NO:12:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:12:

```
Met Pro Arg Leu Phe Phe Phe His Leu Leu Gly Val Cys Leu Leu Leu
 1               5                  10                  15

Asn Gln Phe Ser Arg Ala Val Ala Asp Ser Trp Met Glu Glu Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
 50                  55                  60

Thr Pro Arg Pro Val Ala Glu Ile Val Pro Ser Phe Ile Asn Lys Asp
65                  70                  75                  80

Thr Glu Thr Ile Asn Met Met Ser Glu Phe Val Ala Asn Leu Pro Gln
                85                  90                  95

Glu Leu Lys Leu Thr Leu Ser Glu Met Gln Pro Ala Leu Pro Gln Leu
            100                 105                 110

Gln Gln His Val Pro Val Leu Lys Asp Ser Ser Leu Leu Phe Glu Glu
        115                 120                 125

Phe Lys Lys Leu Ile Arg Asn Arg Gln Ser Glu Ala Ala Asp Ser Ser
 130                 135                 140

Pro Ser Glu Leu Lys Tyr Leu Gly Leu Asp Thr His Ser Arg Lys Lys
145                 150                 155                 160

Arg Gln Leu Tyr Ser Ala Leu Ala Asn Lys Cys Cys His Val Gly Cys
```

```
                        165                 170                 175

Thr Lys Arg Ser Leu Ala Arg Phe Cys
            180                 185

(2) INFORMATION FOR SEQ ID NO:13:

(i) SEQUENCE CHARACTERISTICS:
        (A) LENGTH: 185 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:13:

Met Pro Arg Leu Phe Leu Phe His Leu Leu Glu Phe Cys Leu Leu Leu
 1               5                   10                  15

Asn Gln Phe Ser Arg Ala Val Ala Ala Lys Trp Lys Asp Asp Val Ile
            20                  25                  30

Lys Leu Cys Gly Arg Glu Leu Val Arg Ala Gln Ile Ala Ile Cys Gly
        35                  40                  45

Met Ser Thr Trp Ser Lys Arg Ser Leu Ser Gln Glu Asp Ala Pro Gln
50                  55                  60

Thr Pro Arg Pro Val Ala Glu Ile Val Pro Ser Phe Ile Asn Lys Asp
65                  70                  75                  80

Thr Glu Thr Ile Ile Ile Met Leu Glu Phe Ile Ala Asn Leu Pro Pro
                85                  90                  95

Glu Leu Lys Ala Ala Leu Ser Glu Arg Gln Pro Ser Leu Pro Glu Leu
            100                 105                 110

Gln Gln Tyr Val Pro Ala Leu Lys Asp Ser Asn Leu Ser Phe Glu Glu
        115                 120                 125

Phe Lys Lys Leu Ile Arg Asn Arg Gln Ser Glu Ala Ala Asp Ser Asn
130                 135                 140

Pro Ser Glu Leu Lys Tyr Leu Gly Leu Asp Thr His Ser Gln Lys Lys
145                 150                 155                 160

Arg Arg Pro Tyr Val Ala Leu Phe Glu Lys Cys Cys Leu Ile Gly Cys
                165                 170                 175

Thr Lys Arg Ser Leu Ala Lys Tyr Cys
            180                 185

(2) INFORMATION FOR SEQ ID NO:14:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:14:

Met Asp Pro Arg Leu Pro Ala Trp Ala Leu Val Leu Leu Gly Pro Ala
 1               5                   10                  15

Leu Val Phe Ala Leu Gly Pro Ala Pro Thr Pro Glu Met Arg Glu Lys
            20                  25                  30

Leu Cys Gly His His Phe Val Arg Ala Leu Val Arg Val Cys Gly Gly
        35                  40                  45

Pro Arg Trp Ser Thr Glu Ala Arg Arg Pro Ala Ala Gly Gly Asp Leu
50                  55                  60
```

```
Pro Gln Thr Ser His His Arg His His Arg Ala Ala Ala Thr Asn
65              70                  75                  80

Pro Ala Arg Tyr Cys Cys Leu Ser Gly Cys Thr Gln Gln Asp Leu Leu
                85                  90                  95

Thr Leu Cys Pro Tyr
            100
```

(2) INFORMATION FOR SEQ ID NO:15:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: None (xi) SEQUENCE DESCRIPTION: SEQ ID NO:15:

```
Met Ala Ser Leu Phe Arg Ser Tyr Leu Pro Ala Ile Trp Leu Leu Leu
1               5                   10                  15

Ser Gln Leu Leu Arg Glu Ser Leu Ala Ala Glu Leu Arg Gly Cys Gly
                20                  25                  30

Pro Arg Phe Gly Lys His Leu Leu Ser Tyr Cys Pro Met Pro Glu Lys
            35                  40                  45

Thr Phe Thr Thr Thr Pro Gly Gly Trp Leu Leu Glu Ser Gly Arg Pro
50                  55                  60

Lys Glu Met Val Ser Thr Ser Asn Asn Lys Asp Gly Gln Ala Leu Gly
65              70                  75                  80

Thr Thr Ser Glu Phe Ile Pro Asn Leu Ser Pro Glu Leu Lys Lys Pro
                85                  90                  95

Leu Ser Glu Gly Gln Pro Ser Leu Lys Lys Ile Ile Leu Ser Arg Lys
            100                 105                 110

Lys Arg Ser Gly Arg His Arg Phe Asp Pro Phe Cys Cys Glu Val Ile
            115                 120                 125

Cys Asp Asp Gly Thr Ser Val Lys Leu Cys Thr
130                 135
```

(2) INFORMATION FOR SEQ ID NO:16:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: None (ix) FEATURE:
        (A) NAME/KEY: Other
        (B) LOCATION: 1...1
        (D) OTHER INFORMATION: Xaa is Leu or Gly
        (A) NAME/KEY: Other
        (B) LOCATION: 4...13
        (D) OTHER INFORMATION: Xaa is any amino acid except Cys (xi) SEQUENCE DESCRIPTION: SEQ ID NO:16:

```
Xaa Cys Gly Xaa Xaa Xaa Xaa Xaa Xaa Xaa Xaa Xaa Xaa Cys
1               5                   10
```

(2) INFORMATION FOR SEQ ID NO:17:

(i) SEQUENCE CHARACTERISTICS:
        (A) LENGTH: 15 amino acids
        (B) TYPE: amino acid

```
      (C) STRANDEDNESS: single
      (D) TOPOLOGY: linear (ii) MOLECULE TYPE: None (ix) FEATURE:
      (A) NAME/KEY: Other
      (B) LOCATION: 3...14
      (D) OTHER INFORMATION: Xaa is any amino acid except Cys (xi) SEQUENCE DESCRIPTION: SEQ ID NO:17:

Cys Cys Xaa Xaa Xaa Cys Xaa Xaa Xaa Xaa Xaa Xaa Xaa Xaa Cys
1               5                  10                  15
```

POLYNUCLEOTIDES ENCODING INSULIN HOMOLOG ZINS3

REFERENCE TO RELATED APPLICATIONS

This application is related to Provisional Application 60/028,177, filed on Oct. 15, 1996. Under 35 U.S.C. § 119(e)(1), this application claims benefit of said Provisional Application.

BACKGROUND OF THE INVENTION

Proliferation and differentiation of cells within multicellular organisms is controlled by hormones and polypeptide growth factors. These diffusable molecules allow cells to communicate with each other and act in concert to form organs, and to repair and regenerate damaged tissue. Examples of hormones and growth factors include the steroid hormones (e.g., estrogen, testosterone), parathyroid hormone (PTH), follicle stimulating hormone (FSH), the interleukins, platelet derived growth factor (PDGF), epidermal growth factor (EGF), granulocyte-macrophage colony stimulating factor (GM-CSF), erythropoietin (EPO), insulin and calcitonin.

Hormones and growth factors influence cellular metabolism by binding to receptors. Receptors may be integral membrane proteins that are linked to signalling pathways within the cell, such as second messenger systems. Other classes of receptors are soluble molecules, such as certain transcription factors.

Insulin belongs to a group of protein/polypeptide hormones. Insulin increases the rate of synthesis of glycogen, fatty acids, and proteins and stimulates glycolysis and cell proliferation. It also promotes the transport of glucose, and some other sugars, and amino acids into muscle and fat cells. The mature form of insulin consists of a 30 amino acid residue B chain, that is at the N-terminus of the propeptide form, and a 21 amino acid residue A chain, that is C-terminal. Proinsulin also contains a connecting peptide between the B chain and A chain that is cleaved out to form mature insulin. The B chain and A chain are covalently joined by two disulfide bonds. The B-chain, C-peptide, A-chain motif is found in several other proteins, including relaxin (U.S. Pat. No. 4,835,251), insulin-like growth factors (IGF) I and II (Bang and Hall, In "Insulin-like Growth Factors", P. N. Schofield (eds.), 151–177, Oxford University Press, Oxford, 1992), Leydig Factor (Bullesbach et al., *J. Biol. Chem.* 270:16011–16015, 1995, and early placenta insulin-like factor (EPIL; Chassin et al., *Genomics* 29:465–470, 1995). Unlike other members of the insulin superfamily, IGF I and IGF II have D and E domains that are cleaved post-translationally. Cysteines that are involved in disulfide bonds are conserved in all the memebers of the family and play a role in the tertiary structure of the molecules.

Another member of the insulin-family, relaxin, was recognized from crude extracts of sow corpora lutea (Hisaw, *Proc. Soc. Exp. Biol. Med.* 23:661, 1962 and Fevold et al., *J. Am. Chem. Soc.* 52:3340, 1930) and known to be involved in pregnancy and parturition. Relaxin has been identified in humans, and found to most abundant in the corpora lutea of pregnancy, but is also found in male seminal fluid (Weisse, *Ann. Rev. Physiolog.* 46:43–52, 1984). The relaxins of various species are divergent, with only 50% or less sequence homology between porcine, rat, shark and human relaxins. Within human species, there are two relaxin isoforms that have been identified (Hudson et al., *Nature* 301:628, 1983 and U. S. Pat. No. 4,758,516), however, only one of the mRNA from the isoforms (H2) has been identified in corpora lutea.

Like proinsulin, the B chain-C peptide-A chain motif is recapitulated in the relaxins. Preprorelaxin and preproinsulin both have a signal sequence, followed by the B chain, C peptide, A chain. The mature molecule of both proteins has the signal peptide and C peptide removed with the B and A chains joined by both inter- and intra-chain disulfide bonds (James et al., *Nature* 267:544–546, 1977). It has been postulated that the relaxins play roles in ripening of the cervix, thickening of the endometrium and increasing vascularization of the pregnant uterus and enhancing motility of sperm (U.S. Pat. No. 4,835,251). In addition, relaxin H2 was been found to bind in rat heart and has been tested for treatment of heart failure (U.S. Pat. No. 5,478,807).

Potential therapeutics and tools for identification of therapeutics that exhibit some tissue specificity are very valuable. Members of the insulin family are known to be potent growth factors. Therefore, a novel member of this family, with some specificity would be very valuable for understanding and regulating diseases associated with expression of these proteins.

SUMMARY OF THE INVENTION

The present invention provides an isolated polynucleotide molecule encoding a zins3 polypeptide selected from the group consisting of: (a) polynucleotide molecules comprising a nucleotide sequence as shown in SEQ ID NO: 1 from nucleotide 161 to nucleotide 199 and from nucleotide 437 to nucleotide 481; (b) polynucleotide molecules comprising a nucleotide sequence as shown in SEQ ID NO: 5 from nucleotide 136 to nucleotide 174 and from nucleotide 412 to nucleotide 457; and (c) polynucleotide molecules comprising a nucleotide sequence that encodes a polypeptide that is at least 80% identical to the amino acid sequence of SEQ ID NO: 2 from amino acid residue 29 (Cys) to residue 41 (Cys) and amino acid residue 121 (Cys) to residue 135 (Cys).

In another embodiment, the present invention provides an isolated polynucleotide molecule encoding a polypeptide selected from the group consisting of: (a) polynucleotide molecules comprising a nucleotide sequence as shown in SEQ ID NO: 1 from nucleotide 143 to nucleotide 220 and from nucleotide 419 to nucleotide 481; (b) polynucleotide molecules comprising a nucleotide sequence as shown in SEQ ID NO: 5 from nucleotide 118 to nucleotide 195 and from nucleotide 397 to nucleotide 457; (c) polynucleotide molecules comprising a nucleotide sequence that encodes a polypeptide that is at least 60% identical to the amino acid sequence of SEQ ID NO: 2 from amino acid residue 23 (Lys) to residue 48 (Arg) and from amino acid residue 115 (Gln) to residue 135 (Cys); and (d) polynucleotide molecules comprising a nucleotide sequence as shown in SEQ ID NO: 7 from nucleotide 67 to nucleotide 144 and from nucleotide 343 to nucleotide 405.

In another embodiment, the present invention provides an isolated polynucleotide molecule encoding a polypeptide selected from the group consisting of: (a) polynucleotide molecules comprising a nucleotide sequence as shown in SEQ ID NO: 1 from nucleotide 17 or nucleotide 143 to nucleotide 481; (b) polynucleotide molecules comprising a nucleotide sequence as shown in SEQ ID NO: 5 from nucleotide 52 or nucleotide 118 to nucleotide 457; (c) polynucleotide molecules comprising a nucleotide sequence that encodes a polypeptide that is at least 60% identical to the amino acid sequence of SEQ ID NO: 2 from amino acid residue 1 (Met) or residue 23 (Lys) to residue 135 (Cys); and (d) polynucleotide molecules comprising a nucleotide sequence as shown in SEQ ID NO: 7 from nucleotide 1 or nucleotide 67 to nucleotide 405.

In another embodiment, the present invention provides an isolated polynucleotide molecule encoding a polypeptide selected from the group consisting of: (a) polynucleotide molecules comprising a nucleotide sequence as shown in SEQ ID NO: 1 from nucleotide 1 to nucleotide 792; and (b) polynucleotide molecules comprising a nucleotide sequence as shown in SEQ ID NO: 5 from nucleotide 1 to nucleotide 735.

In another aspect, the present invention provides an expression vector comprising the following operably linked elements: a transcription promoter; a DNA segment selected from the group consisting of: (a) polynucleotide molecules comprising a nucleotide sequence as shown in SEQ ID NO: 1 from nucleotide 161 to nucleotide 199 and from nucleotide 437 to nucleotide 481; (b) polynucleotide molecules comprising a nucleotide sequence as shown in SEQ ID NO: 5 from nucleotide 136 to nucleotide 174 and from nucleotide 412 to nucleotide 457; and (c) polynucleotide molecules comprising a nucleotide sequence that encodes a polypeptide that is at least 60% identical to the amino acid sequence of SEQ ID NO: 2 from amino acid residue 29 (Cys) to residue 41 (Cys) and amino acid residue 121 (Cys) to residue 135 (Cys); and a transcription terminator.

In another aspect, the present invention provides a cultured cell into which has been introduced an expression vector comprising the following operably linked elements: a transcription promoter; a DNA segment selected from the group consisting of: (a) polynucleotide molecules comprising a nucleotide sequence as shown in SEQ ID NO: 1 from nucleotide 161 to nucleotide 199 and from nucleotide 437 to nucleotide 481; (b) polynucleotide molecules comprising a nucleotide sequence as shown in SEQ ID NO: 5 from nucleotide 136 to nucleotide 174 and from nucleotide 412 to nucleotide 457; and (c) polynucleotide molecules comprising a nucleotide sequence that encodes a polypeptide that is at least 60% identical to the amino acid sequence of SEQ ID NO: 2 from amino acid residue 29 (Cys) to residue 41 (Cys) and amino acid residue 121 (Cys) to residue 135 (Cys); and a transcription terminator, wherein said cell expresses an insulin homolog polypeptide encoded by the DNA segment.

In another embodiment of the present invention, the cell contains a second expression vector that has a DNA segment that encodes for a heterologous processing enzyme.

Another aspects of the present invention provides methods for producing an insulin homolog polypeptides comprising: culturing a cell into which has been introduced an expression vector according to claim 5, whereby said cell expresses an insulin homolog polypeptide; and recovering the insulin homolog polypeptide.

Another aspect of the present invention provides, isolated insulin homolog polypeptides selected from the group consisting of: (a) polypeptide molecules comprising a first polypeptide comprising a polypeptide as shown in SEQ ID NO: 2 from amino acid residue 29 (Cys) to residue 41 (Cys) and a second polypeptide comprising a polypeptide as shown in SEQ ID NO: 2 from amino acid residue 121 (Cys) to residue 135 (Cys); and (b) polypeptide molecules comprising a first polypeptide comprising a polypeptide as shown in SEQ ID NO: 6 from amino acid residue 29 (Cys) to residue 41 (Cys) and a second polypeptide comprising a polypeptide as shown in SEQ ID NO: 6 from amino acid residue 121 (Cys) to residue 135 (Cys), wherein said first polypeptide and said second polypeptide are capable of associating through cysteine bridges.

In another embodiment, the present invention provides an isolated insulin homolog polypeptide selected from the group consisting of: (a) polypeptide molecules comprising a first polypeptide comprising a polypeptide as shown in SEQ ID NO: 2 from amino acid residue 23 (Lys) to residue 46 (Trp) and a second polypeptide comprising a polypeptide as shown in SEQ ID NO: 2 from amino acid residue 115 (Gln) to residue 135 (Cys); (b) polypeptide molecules comprising a first polypeptide comprising a polypeptide as shown in SEQ ID NO: 6 from amino acid residue 23 (Arg) to residue 46 (Trp) and a second polypeptide comprising a polypeptide as shown in SEQ ID NO: 6 from amino acid residue 116 (Asp) to residue 135 (Cys); (c) polypeptide molecules that are at least 80% identical to the amino acid sequences of (a) or (b), wherein said first polypeptide and said second polypeptide are capable are capable of associating through cysteine bridges.

An embodiment of the present invention provides an isolated insulin homolog polypeptide selected from the group consisting of: (a) polypeptide molecules comprising an amino acid sequence from residue 1 (Met) or 23 (Lys) to residue 135 (Cys) as shown in SEQ ID NO: 2; (b) polypeptide molecules comprising an amino acid sequence from residue 1 (Met) or 23 (Arg) to residue 135 (Cys) as shown in SEQ ID NO: 6; and (c) polypeptide molecules that are at least 80% identical to the amino acid sequences of (a) or (b).

Another embodiment provides, isolated insulin homolog polypeptide wherein the polypeptide, upon processing, is capable of forming a disulfide associated first and second polypeptide, wherein the first polypeptide comprises a polypeptide as shown in SEQ ID NO: 2 from amino acid residue 23 (Lys) to residue 46 (Trp) and the second polypeptide comprises a polypeptide as shown in SEQ ID NO: 2 from amino acid residue 115 (Gln) to residue 135 (Cys); or the first polypeptide comprises a polypeptide as shown in SEQ ID NO: 6 from amino acid residue 23 (Arg) to residue 46 (Trp) and the second polypeptide comprises a polypeptide as shown in SEQ ID NO: 6 from amino acid residue 116 (Asp) to residue 135 (Cys).

In another aspect, the present invention provides non-human mammals into the germ line of which has been introduced a heterologous DNA segment selected from the group consisting of: (a) polynucleotide molecules comprising a nucleotide sequence as shown in SEQ ID NO: 1 from nucleotide 143 to nucleotide 220 and from nucleotide 419 to nucleotide 481; (b) polynucleotide molecules comprising a nucleotide sequence as shown in SEQ ID NO: 5 from nucleotide 118 to nucleotide 195 and from nucleotide 397 to nucleotide 457; (c) polynucleotide molecules comprising a nucleotide sequence that encodes a polypeptide that is at least 60% identical to the amino acid sequence of SEQ ID NO: 2 from amino acid residue 23 (Lys) to residue 48 (Arg) and from amino acid residue 115 (Gln) to residue 135 (Cys); and (d) polynucleotide molecules comprising a nucleotide sequence as shown in SEQ ID NO: 7 from nucleotide 67 to nucleotide 144 and from nucleotide 343 to nucleotide 405, wherein said mammal produces an insulin homolog polypeptide encoded by said DNA segment.

In another aspect, the present invention provides methods of producing insulin homolog polypeptides comprising:

collecting a body fluid from a non-human mammal wherein said body fluid contains the insulin homolog polypeptide encoded by the DNA segment; and recovering the insulin homolog polypeptide.

In another aspect, the present invention provides antibodies that bind to an epitope of a insulin homolog polypeptide.

In another aspect, the present invention provides probes which comprise an oligonucleotide of at least 12 nucleotides corresponding to nucleotide 158 to nucleotide 199 of SEQ ID NO: 1 and nucleotide 437 to nucleotide 481 of SEQ ID NO: 1.

BRIEF DESCRIPTION OF THE DRAWINGS

FIG. 1 is a multiple alignment of human IGF I (SEQ ID NO: 9), human IGF II (SEQ ID NO: 10), human insulin (SEQ ID NO: 11), human relaxin 2 (SEQ ID NO: 12), human relaxin 1 (SEQ ID NO: 13), human Leydig Factor (INL3 hu or HSLILH (SEQ ID NO: 14)), human INSL4 (also known as early placenta insulin-like factor or EPIL (SEQ ID NO: 15)) human Zins3 (SEQ ID NO: 2), and mouse Zins3 (SEQ ID NO: 6).

DETAILED DESCRIPTION OF THE INVENTION

Figure 2:
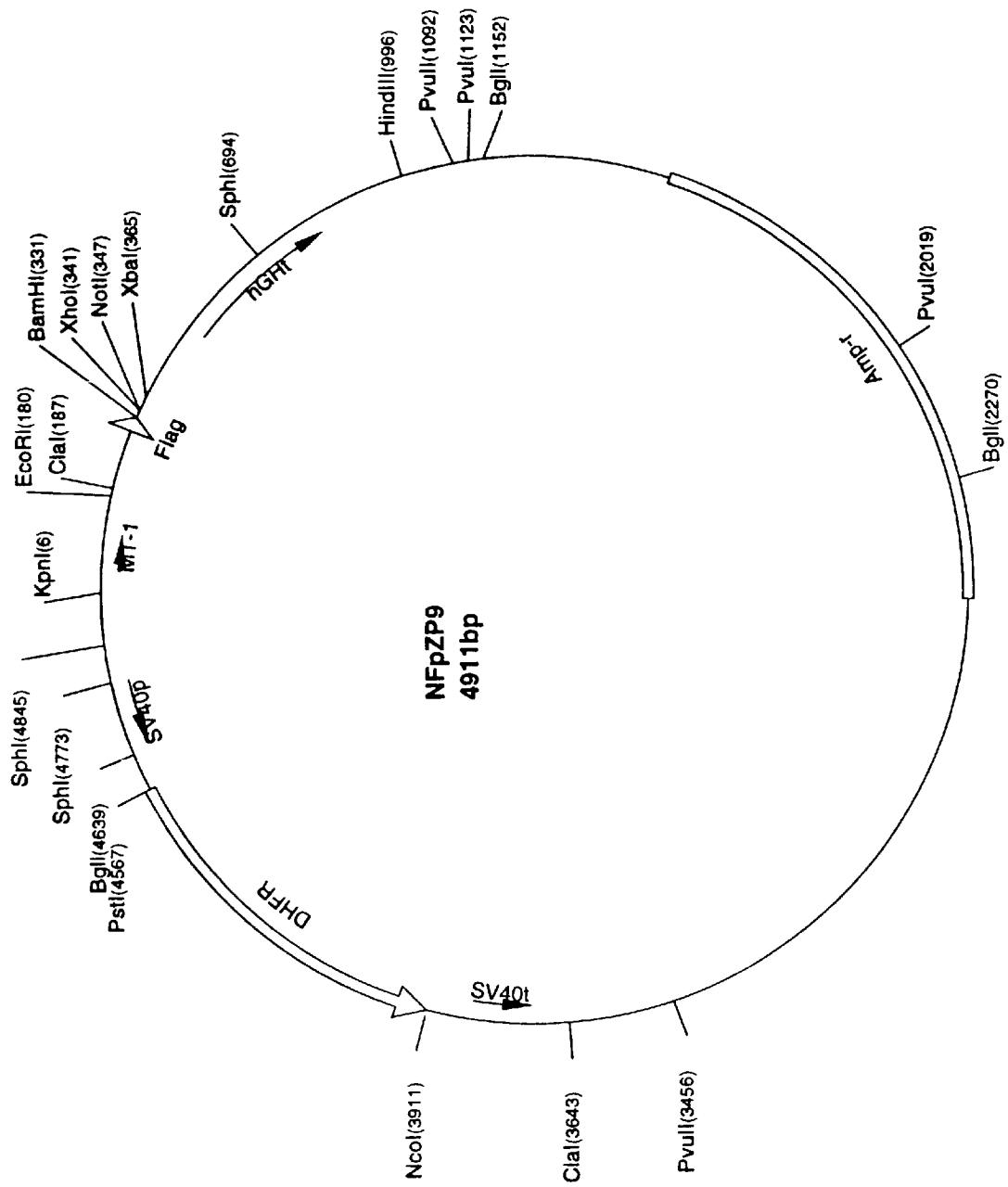
FIG. 2 is an illustration of the mammalian expression vector NFpZP9.

The term "allelic variant" is used herein to denote any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

The term "expression vector" is used to denote a DNA molecule, linear or circular, that comprises a segment encoding a polypeptide of interest operably linked to additional segments that provide for its transcription. Such additional segments include promoter and terminator sequences, and may also include one or more origins of replication, one or more selectable markers, an enhancer, a polyadenylation signal, etc. Expression vectors are generally derived from plasmid or viral DNA, or may contain elements of both.

The term "isolated", when applied to a polynucleotide, denotes that the polynucleotide has been removed from its natural genetic milieu and is thus free of other extraneous or unwanted coding sequences, and is in a form suitable for use within genetically engineered protein production systems.

"Operably linked", when referring to DNA segments, indicates that the segments are arranged so that they function in concert for their intended purposes, e.g. transcription initiates in the promoter and proceeds through the coding segment to the terminator.

A "polynucleotide" is a single- or double-stranded polymer of deoxyribonucleotide or ribonucleotide bases read from the 5' to the 3' end. Polynucleotides include RNA and DNA, and may be isolated from natural sources, synthesized in vitro, or prepared from a combination of natural and synthetic molecules.

The term "promoter" is used herein for its art-recognized meaning to denote a portion of a gene containing DNA sequences that provide for the binding of RNA polymerase and initiation of transcription. Promoter sequences are commonly, but not always, found in the 5' non-coding regions of genes.

The term "receptor" is used herein to denote a cell-associated protein, or a polypeptide subunit of such a protein, that binds to a bioactive molecule (the "ligand") and mediates the effect of the ligand on the cell. Binding of ligand to receptor results in a conformational change in the receptor (and, in some cases, receptor multimerization, i.e., association of identical or different receptor subunits) that causes interactions between the effector domain(s) and other molecule(s) in the cell. These interactions in turn lead to alterations in the metabolism of the cell. Metabolic events that are linked to receptor-ligand interactions include gene transcription, phosphorylation, dephosphorylation, cell proliferation, increases in cyclic AMP production, mobilization of cellular calcium, mobilization of membrane lipids, cell adhesion, hydrolysis of inositol lipids and hydrolysis of phospholipids. The term "receptor polypeptide" is used to denote complete receptor polypeptide chains and portions thereof, including isolated functional domains (e.g., ligand-binding domains).

A "secretory signal sequence" is a DNA sequence that encodes a polypeptide (a "secretory peptide") that, as a component of a larger polypeptide, directs the larger polypeptide through a secretory pathway of a cell in which it is synthesized. The larger polypeptide is commonly cleaved to remove the secretory peptide during transit through the secretory pathway.

The term "contig" denotes a polynucleotide segment equivalent in nucleotide sequence to an EST. A "contig assembly" denotes a collection of EST contigs that define a larger polynucleotide segment containing an open reading frame encoding a full-length or partial polypeptide.

The present invention is based in part upon the discovery of a novel DNA sequence that encodes a protein having the structure of an insulin homolog polypeptide, and was designated Zins3. The cDNA library from which this DNA sequence was identified was generated from sigmoid colon tissue of a 40 year-old male with Crohn's disease. Tissue distribution analyses showed that the mRNA for this novel polynucleotide was not expressed in detectable amounts in normal tissue. Thus, the polynucleotide of the present invention is a candidate marker for a disease state and/or specialized cell type.

The DNA sequence was identified by querying an EST database using a cysteine motif found in the B-chain of insulin. Analysis of the human cDNA encoding Zins3 (SEQ ID NO: 1) revealed an open reading frame encoding 135 amino acids (SEQ ID NO: 2), comprising a putative signal sequence and a mature polypeptide. The mature polypeptide has homology with insulin, relaxin 1 and 2, INSL-4 and Leydig Factor, respectively, as shown in FIG. 1. Within this family, the cysteine motif is highly conserved in the B and A chains, where the B chain motif can be represented as [L/G]CGX{10}C (SEQ ID NO:16), where X{ } is the number of any amino acid residues except cysteine. The A chain motif is CCX{3}CX{8}C (SEQ ID NO:17), where X{ } is the number of any amino acid residues, except Cysteine and [L/G] is either Leu or Gly.

Isolation of the human cDNA encoding Zins3 revealed that the predicted amino acid sequence contained the B chain-C peptide-A chain motif found in the relaxins and insulin. Preproinsulin and preprorelaxin both have a signal sequence, followed by the B chain, C peptide, and A chain. The mature molecule of both relaxin and insulin has the signal peptide and C peptide removed, with the B and A chains joined by both inter- and intra- disulfide bonds (James et al., *Nature* 267:544–546, 1977).

Processing of the mature protein molecule involves cleavage at the C-terminus of the signal peptide, and, based on predicted structural homology with other mature members of the insulin family, a cleavage at the C-terminus of the B chain and at the N-terminus of the A chain, resulting in removal of the C-peptide. The mature human polypeptide encoded by the polynucleotide of the present invention comprisesa B chain and A chain, wherein the B chain comprises the amino acid sequence of SEQ ID NO: 2 from amino acid residue 29 (Cys) to residue 41 (Cys), and wherein the A chain comprises the amino sequence of SEQ ID NO: 2 from amino acid residue 121 (Cys) to residue 135 (Cys) that are capable of associating through cysteine bridges and forming disulfide-bonded molecules.

The mature B chain further comprises the amino acid sequence of SEQ ID NO: 2 from amino acid residue 23 (Lys) to residue 48 (Arg), with corresponding nucleotide sequence as shown in SEQ ID NO: 1 from nucleotide 143 to nucleotide 220. It is possible that specific processing enzymes, for example, certain metalloendopeptidases (Chesneasu et al.,*J. Biol. Chem.* 269:2056–2061, 1994) and enzymes for processing somatostatin (Gluschankof, et al., *J. Biol. Chem.* 262:9615–9620, 1987) may cleave at the N-terminus of amino acid residue 47 (Arg) of SEQ ID NO: 2, resulting in Trp residue (amino acid residue 46 of SEQ ID NO: 2) at the C-terminus of the B chain polypeptide. The mature A chain further comprises the amino acid sequence of SEQ ID NO: 2 from amino acid residue 115 (Gln) to residue 135 (Cys), with the corresponding nucleotide sequence shown in SEQ ID NO: 1 from nucleotide 419 to nucleotide 481. Thus, a C-peptide of Zins3 molecules comprises amino acid residue 49 (His) to amino acid residue 114 (Arg) of SEQ ID NO: 2, with the corresponding polynucleotide sequence shown in SEQ ID NO: 1 from nucleotide 221 to nucleotide 418.

Isolation of the mouse cDNA encoding Zins3 confirmed that the predicted amino acid sequence contained the B chain-C peptide-A chain motif as well. The mature B chain further comprises the amino acid sequence of SEQ ID NO: 6 from amino acid residue 23 (Lys) to residue 48 (Arg), with the possibility that specific enzymes may cleave at the N-terminus of amino acid residue 47 (Arg) of SEQ ID NO: 6, resulting in Trp residue (amino acid residue 46 of SEQ ID NO: 2) at the C-terminus of the B chain polypeptide, as described above. The mature A chain further comprises the amino acid sequence of SEQ ID NO: 2 from amino acid residue 116 (Asp) to residue 135 (Cys). Thus, a C-peptide of Zins3 molecules comprises amino acid residue 49 (His) to amino acid residue 115 (Arg) of SEQ ID NO: 6. Corresponding polynucleotide sequence is shown in SEQ ID NO: 5.

The enzymology of proinsulin conversion suggests that prohormone convertase 3 (PC3) or other homolog-monobasic capable convertases, cleave primarily at the B chain-C-peptide junction, and that prohormone convertase 2 (PC2) or similar convertases cleave preferentially at the C-peptide-A-chain junction and favor proinsulin already processed by PC3 over intact prohormone. In human and rat proinsulin, dibasic residues link the B chain and C-peptide and the C-peptide and A chain. In addition, a basic residue 4 residues N-terminal to the cleavage site (a "P4 basic residue") may be present at one or both junctions, and may influence the ability of furin, or similar convertases of the furin family such as prohormone convertase 4 (PC4) and PACE4, to cleave at the junction sites. In a study reported by Vollenweider et al. (*Diabetes* 44:1075–80, 1995), cotransfection of COS cells with PC3 and either human proinsulin, rat proinsulin II or mutant human proinsulin Arg showed that PC3 cleaved both proinsulin junctions, regardless of the presence or absence of a P4 basic residue.

SEQ ID NO: 7 is a degenerate polynucleotide sequence that encompasses all polynucleotides that could encode the Zins3 polypeptide of SEQ ID NO: 2 amino acids 1 or 23 to 135. Thus, Zins3 polypeptide-encoding polynucleotides ranging nucleotide 1 or 69 to nucleotide 405 of SEQ ID NO: 7 are contemplated by the present invention. Also contemplated by the present invention are are fragments and fusions as described above with respect to SEQ ID NO: 1, which are formed from analogous regions of SEQ ID NO: 7.

The symbols in SEQ ID NO: 7 are summarized in Table 1 below:

TABLE 1

| Nucleotide | Resolutions | Complement | Resolutions |
|---|---|---|---|
| A | A | T | T |
| C | C | G | G |
| G | G | C | C |
| T | T | A | A |
| R | A\|G | Y | C\|T |
| Y | C\|T | R | A\|G |
| M | A\|C | K | G\|T |
| K | G\|T | M | A\|C |
| S | C\|G | S | C\|G |
| C\|G | A\|T | W | A\|T |
| H | A\|C\|T | D | A\|G\|T |
| B | C\|G\|T | V | A\|C\|G |
| V | A\|C\|G | B | C\|G\|T |
| D | A\|G\|T | H | A\|C\|T |
| N | A\|C\|G\|T | N | A\|C\|G\|T |

The degenerate codons used in SEQ ID NO: 3, encompassing all possible codons for a given amino acid, are set forth in Table 2 below.

TABLE 2

| Amino Acid | Letter | Codons | Degenerate Codon |
|---|---|---|---|
| Cys | C | TGC TGT | TGY |
| Ser | S | AGC AGT TCA TCC TCG TCT | WSN |
| Thr | T | ACA ACC ACG ACT | ACN |
| Pro | P | CCA CCC CCG CCT | CCN |
| Ala | A | GCA GCC GCG GCT | GCN |
| Gly | G | GGA GGC GGG GGT | GGN |
| Asn | N | AAC AAT | AAY |
| Asp | D | GAC GAT | GAY |
| Glu | E | GAA GAG | GAR |
| Gln | Q | CAA CAG | CAR |
| His | H | CAC CAT | CAY |
| Arg | R | AGA AGG CGA CGC CGG CGT | MGN |
| Lys | K | AAA AAG | AAR |
| Met | M | ATG | ATG |
| Ile | I | ATA ATC ATT | ATH |
| Leu | L | CTA CTC CTG CTT TTA TTG | YTN |
| Val | V | GTA GTC GTG GTT | GTN |
| Phe | F | TTC TTT | TTY |
| Tyr | Y | TAC TAT | TAY |
| Trp | W | TGG | TGG |
| Ter | — | TAA TAG TGA | TRR |
| Asn\|Asp | B | | RAY |
| Glu\|Gln | Z | | SAR |
| Any | X | | NNN |
| Gap | — | — | |

One of ordinary skill in the art will appreciate that some ambiguity is introduced in determining a degenerate codon, representative of all possible codons encoding each amino acid. For example, the degenerate codon for serine (WSN) can, in some circumstances, encode arginine (AGR), and the degenerate codon for arginine (MGN) can, in some circumstances, encode serine (AGY). A similar relationship exists between codons encoding phenylalanine and leucine. Thus, some polynucleotides encompassed by the degenerate sequence may have some incorrect amino acids, but one of ordinary skill in the art can easily identify such erroneous sequences by reference to the amino acid sequence of SEQ ID NO: 2.

Those skilled in the art will recognize that that sequences disclosed in SEQ ID NO: 1 and 5 represent a single allele of the human and mouse Zins3 gene and polypeptide, respectively, and that allelic variation and alternative splicing are expected to occur. Allelic variants can be cloned by probing cDNA or genomic libraries from different individuals according to standard procedures. Allelic variants of the DNA sequence shown in SEQ ID NO: 2 and 6, including those containing silent mutations and those in which mutations result in amino acid sequence changes, are within the scope of the present invention, as are proteins which are allelic variants of SEQ ID NO: 2 and 6.

The present invention further provides counterpart polypeptides and polynucleotides from other species ("species homologs"). Of particular interest are zins3 polypeptides from other mammalian species, including murine, porcine, ovine, bovine, canine, feline, equine and other primate proteins.

Species homologs of the human proteins can be cloned using information and compositions provided by the present invention in combination with conventional cloning techniques. For example, a cDNA can be cloned using mRNA obtained from a tissue or cell type that expresses the protein. Suitable sources of mRNA can be identified by probing Northern blots with probes designed from the sequences disclosed herein. A library is then prepared from mRNA of a positive tissue of cell line. A zins3-encoding cDNA can then be isolated by a variety of methods, such as by probing with a complete or partial human cDNA or with one or more sets of degenerate probes based on the disclosed sequences. A cDNA can also be cloned using the polymerase chain reaction, or PCR (Mullis, U.S. Pat. No. 4,683,202), using primers designed from the sequences disclosed herein. Within an additional method, the cDNA library can be used to transform or transfect host cells, and expression of the cDNA of interest can be detected with an antibody to the zins3 or a bioassay. Similar techniques can also be applied to the isolation of genomic clones.

Within preferred embodiments of the invention the isolated polynucleotides will serve as a probe and hybridize to similar sized regions of SEQ ID NO: 1 or a sequence complementary thereto, under stringent conditions. Such probes will be at least 12 nucleotides, preferably 25 nucleotides, and most preferably 40 nucleotides in length. In a particularly preferred embodiment, oligonucleotide probes corresponding to polynucleotides 158 to 199 of SEQ ID NO: 1 and 437 to 481 of SEQ ID NO: 1, are used to identify new members of the insulin homolog family. In general, stringent conditions are selected to be about 5° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Typical stringent conditions are those in which the salt concentration is at least about 0.02 M at pH 7 and the temperature is at least about 60° C.

The present invention also provides isolated zins3 polypeptides that are substantially homologous to the polypeptides of SEQ ID NO: 2 and their species homologs. By "isolated" is meant a protein or polypeptide which is found in a condition other than its native environment, such as apart from blood and animal tissue. In a preferred form, the isolated polypeptide is substantially free of other polypeptides, particularly other polypeptides of animal origin. It is preferred to provide the polypeptides in a highly purified form, i.e. greater than 95% pure, more preferably greater than 99% pure. The term "substantially homologous" is used herein to denote polypeptides having 50%, preferably 60%, more preferably at least 80%, sequence identity to the sequences shown in SEQ ID NO: 2 or their species homologs. Such polypeptides will more preferably be at least 90% identical, and most preferably 95% or more identical to SEQ ID NO: 2 or their species homologs. Percent sequence identity is determined by conventional methods. See, for example, Altschul et al., *Bull. Math. Bio.* 48: 603–616, 1986 and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 3 (amino acids are indicated by the standard one-letter codes).

TABLE 3

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -1 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

The percent identity is then calculated as:

$$\frac{\text{Total number of identical matches}}{[\text{length of the longer sequence plus the number of gaps introduced into the longer sequence in order to align the two sequences}]} \times 100$$

Sequence identity of polynucleotide molecules is determined by similar methods using a ratio as disclosed above.

Substantially homologous proteins and polypeptides are characterized as having one or more amino acid substitutions, deletions or additions. These changes are preferably of a minor nature, that is conservative amino acid substitutions (see Table 4) and other substitutions that do not significantly affect the folding or activity of the protein or polypeptide; small deletions, typically of one to about 30 amino acids; and small amino- or carboxyl-terminal extensions, such as an amino-terminal methionine residue, a small linker peptide of up to about 20–25 residues, or a small extension that facilitates purification, (an affinity tag), such as a poly-histidine tract, protein A (Nilsson et al., *EMBO J.* 4:1075, 1985; Nilsson et al., *Methods Enzymol.* 198:3, 1991), glutathione S transferase (Smith and Johnson, *Gene* 67:31, 1988), maltose binding protein (Kellerman and Ferenci, *Methods Enzymol.* 90:459–463, 1982; Guan et al., *Gene* 67:21–30, 1987), or other antigenic epitope or binding domain. See, in general Ford et al., *Protein Expression and Purification* 2: 95–107, 1991, which is incorporated herein by reference. DNAs encoding affinity tags are available from commercial suppliers (e.g., Pharmacia Biotech, Piscataway, N.J.; New England Biolabs, Beverly, Mass.).

TABLE 4

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

The proteins of the present invention can also comprise, in addition to the 20 standard amino acids, non-naturally occurring amino acid residues. Non-naturally occurring amino acids include, without limitation, trans-3-methylproline, 2,4-methanoproline, cis-4-hydroxyproline, trans-4-hydroxyproline, N-methyl-glycine, allo-threonine, methylthreonine, hydroxyethyl-cysteine, hydroxyethylhomocysteine, nitroglutamine, homoglutamine, pipecolic acid, tert-leucine, norvaline, 2-azaphenylalanine, 3-azaphenylalanine, 4-azaphenylalanine, 4-fluorophenylalanine, 4-hydroxyproline, 6-N-methyl lysine, 2-aminoisobutyric acid, isovaline and α-methyl serine. Several methods are known in the art for incorporating non-naturally occurring amino acid residues into proteins. For example, an in vitro system can be employed wherein nonsense mutations are suppressed using chemically aminoacylated suppressor tRNAs. Methods for synthesizing amino acids and aminoacylating tRNA are known in the art. Transcription and translation of plasmids containing nonsense mutations are carried out in a cell free system comprising an *E. coli* S30 extract and commercially available enzymes and other reagents. Proteins are purified by chromatography. See, for example, Robertson et al., *J. Am. Chem. Soc.* 113:2722, 1991; Ellman et al., *Meth. Enzymol.* 202:301, 1991; Chung et al., *Science* 259:806–09, 1993; and Chung et al., *Proc. Natl. Acad. Sci. USA* 90:10145–49, 1993). In a second method, translation is carried out in Xenopus oocytes by microinjection of mutated mRNA and chemically aminoacylated suppressor tRNAs (Turcatti et al., *J. Biol. Chem.* 271:19991–98, 1996). Within a third method, *E. coli* cells are cultured in the absence of a natural amino acid that is to be replaced (e.g., phenylalanine) and in the presence of the desired non-naturally occurring amino acid(s) (e.g., 2-azaphenylalanine, 3-azaphenylalanine, 4-azaphenylalanine, or 4-fluorophenylalanine). The non-naturally occurring amino acid is incorporated into the protein in place of its natural counterpart. See, Koide et al., *Biochem.* 33:7470–76, 1994. Naturally occurring amino acid residues can be converted to non-naturally occurring species by in vitro chemical modification. Chemical modification can be combined with site-directed mutagenesis to further expand the range of substitutions (Wynn and Richards, *Protein Sci.* 2:395–403, 1993). Based on homology with other members of the relaxin family, amino acid residue 115 (Gln) of SEQ ID NO: 2 is putatively converted to 5-oxopyrrolidone carboxylic acid.

Tertiary structure of insulin, and homologs in the insulin family, comprises three helices, designated B, A1 and A2, respectively, and shown in FIG. 1 as bolded and italized areas. Based on homology with other members of the insulin family, amino acid residue 35 (Arg) of SEQ ID NO: 2 is predicted to play a role in receptor binding.

Essential amino acids in the polypeptides of the present invention can be identified according to procedures known in the art, such as site-directed mutagenesis or alanine-scanning mutagenesis (Cunningham and Wells, *Science* 244, 1081–1085, 1989). In the latter technique, single alanine mutations are introduced at every residue in the molecule, and the resultant mutant molecules are tested for biological activity to identify amino acid residues that are critical to the activity of the molecule. Sites of ligand-receptor interaction can also be determined by physical analysis of structure, as determined by such techniques as nuclear magnetic resonance, crystallography, electron diffraction or photoaffinity labeling, in conjunction with mutation of putative contact site amino acids. See, for example, de Vos et al., *Science* 255:306–312, 1992; Smith et al., *J. Mol. Biol.* 224:899–904, 1992; Wlodaver et al., *FEBS Lett.* 309:59–64, 1992. The identities of essential amino acids can also be inferred from analysis of homologies with related insulin family members.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., *Biochem.* 30:10832–10837, 1991; Ladner et al., U.S. Pat. No. 5,223,409; Huse, WIPO Publication WO 92/06204) and region-directed mutagenesis (Derbyshire et al., *Gene* 6:145, 1986; Ner et al., *DNA* 7:127, 1988).

Mutagenesis methods as disclosed above can be combined with high-throughput, automated screening methods to detect activity of cloned, mutagenized polypeptides in host cells. Mutagenized DNA molecules that encode active polypeptides can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to residues 1 or 23 to 135 of SEQ ID NO: 2, residues 1 or 23 to 135 of SEQ ID NO: 6, or allelic variants thereof and retain the properties of the wild-type protein to stimulate cell proliferation, differentiation and/or metabolic processes.

The polypeptides of the present invention, including full-length proteins and fragments thereof, can be produced in genetically engineered host cells according to conventional techniques. Thus, the present invention includes polypeptides produced by expression of the polynucleotides described herein and shown, for example, in SEQ ID NO: 1 or SEQ ID NO: 5.

Suitable host cells are those cell types that can be transformed or transfected with exogenous DNA and grown in culture, and include bacteria, fungal cells, and cultured higher eukaryotic cells. Eukaryotic cells, particularly culture cells of multicellular organisms, are preferred. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

In general, a DNA sequence encoding a zins3 polypeptide is operably linked to other genetic elements required for its expression, generally including a transcription promoter and terminator, within an expression vector. The vector will also commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

To direct a zins3 polypeptide into the secretory pathway of a host cell, a secretory signal sequence (also known as a leader sequence, prepro sequence or pre sequence) is provided in the expression vector. The secretory signal sequence may be that of the Zins3 polypeptide, or may be derived from another secreted protein (e.g., t-PA) or synthesized de novo. The secretory signal sequence is joined to the zins3 DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are also preferred hosts within the present invention. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), and liposome-mediated transfection (Hawley-Nelson et al., *Focus* 15:73, 1993; Ciccarone et al., *Focus* 15:80, 1993), which are incorporated herein by reference. The production of recombinant polypeptides in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, 10801 University Boulevard, Manassas, Va. 20110-2209. In general, strong transcription promoters are preferred, such as promoters from SV-40 or cytomegalovirus. See, e.g., U.S. Pat. No. 4,956,288. Other suitable promoters include those from metallothionein genes (U.S. Pat. Nos. 4,579,821 and 4,601,978, which are incorporated herein by reference) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multi-drug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of *Agrobacterium rhizogenes* as a vector for expressing genes in plant cells has been reviewed by Sinkar et al., *J. Biosci. (Bangalore)* 11:47–58, 1987.

Fungal cells, including yeast cells, and particularly cells of the genera Saccharomyces and Pichia, can also be used within the present invention, such as for producing Zins3 fragments or polypeptide fusions. Methods for transforming yeast cells with exogenous DNA and producing recombinant polypeptides therefrom are disclosed by, for example, Kawasaki, U.S. Pat. No. 4,599,311; Kawasaki et al., U.S.

Pat. No. 4,931,373; Brake, U.S. Pat. No. 4,870,008; Welch et al., U.S. Pat. No. 5,037,743; and Murray et al., U.S. Pat. No. 4,845,075, which are incorporated herein by reference. Transformed cells are selected by phenotype determined by the selectable marker, commonly drug resistance or the ability to grow in the absence of a particular nutrient (e.g. leucine). A preferred vector system for use in yeast is the POT1 vector system disclosed by Kawasaki et al. (U.S. Pat. No. 4,931,373), which allows transformed cells to be selected by growth in glucose-containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977,092, which are incorporated herein by reference) and alcohol dehydrogenase genes. See also U.S. Pat. Nos. 4,990,446; 5,063,154; 5,139,936 and 4,661,454, which are incorporated herein by reference. Transformation systems for other yeasts, including *Hansenula polymorpha, Schizosaccharomyces pombe, Kluyveromyces lactis, Kluyveromyces fragilis, Ustilago maydis, Pichia pastoris, Pichia guillermondii, Pichia methanolica* (WO 97/17450), and *Candida maltosa* are known in the art. See, for example, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference. Methods for transforming Neurospora are disclosed by Lambowitz, U.S. Pat. No. 4,486,533, which is incorporated herein by reference.

In a preferred embodiment, transformed or transfected host cells are co-transfected with heterologous DNA constructs that express active prohormone convertases that cleave prohormones, such as Zins3 molecules of the present invention, resulting in mature, biologically active polypeptide hormones. Methods for providing constructs and hosts are described in WO 94/20624, and are well known in the art.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Zins3 polypeptides can also be used to prepare antibodies that specifically bind to zins3 epitopes, peptides or polypeptides. Methods for preparing polyclonal and monoclonal antibodies are well known in the art (see, for example, Sambrook et al., *Molecular Cloning: A Laboratory Manual, Second Edition,* Cold Spring Harbor, N.Y. 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one or ordinary skill in the art, polyclonal antibodies can be generated from a variety of warm-blooded animals, such as humans, horses, cows, goats, sheep, dogs, chickens, rabbits, mice and rats.

The immunogenicity of a Zins3 polypeptide may be increased through the use of an adjuvant, such as alum (aluminum hydroxide) or Freund's complete or incomplete adjuvant. Polypeptides useful for immunization also include fusion polypeptides, such as fusions of Zins3 polypeptides or a portion thereof with an immunoglobulin polypeptide or with a maltose binding protein. The polypeptide immunogen may be a full-length molecule or a portion thereof. If the polypeptide portion is "hapten-like", such a portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating ro selecting antibodies useful herein include in vitro exposure of lymphocytes to zins3 polypeptides or peptides, and selection of antibody display libraries in phage or similar vectors (for instance, through use of immobilized or labeled zins3 polypeptide or peptide).

Antibodies are defined to be specifically binding if they bind to a zins3 polypeptide with a binding affinity ($K_a$) of $10^6$ $M^{-1}$ or greater, perferably $10^7$ $M^{-1}$ or greater, and most preferably $10^9$ $M^{-1}$ or greater. The binding affinity of an antibody can be readily determined by one of ordinary skill in the art (for example, by Scatchard analysis).

A variety of assays known to those skilled in the art can be utilized to detect antibodies which specifically bind to zins3 polypeptides or peptides. Exemplary assays are described in detail in *Antibodies: A Laboratory Manual,* Harlow and Lane (Eds.), Cold Spring Harbor Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant zins3 polypeptides or peptides.

Antibodies to zins3 polypeptides may be used for tagging cells that express zins3 polypeptides; for isolating zins3 polypeptides by affinity purification; for diagnostic assays for determining circulating levels of zins3 polypeptides; for detecting or quantitating soluble zins3 polypeptides as marker of underlying pathology or disease; in analytical methods employing FACS; for screening expression libraries; for generating anti-idiotypic antibodies; and as neutralizing antibodies. Suitable direct tags or labels include radionuclides, enzymes, substrates, cofactors, inhibitors, fluorescent markers, chemiluminescent markers, magnetic particles and the like; indirect tags or labels may feature use of biotin-avidin or other complement/anticomplement paris as intermediates. Antibodies herein may also be directly or indirectly conjugated to drugs, toxins, radionuclides and the like, and these conjugates used for in vivo diagnostic or therapeutic applications.

Zins3 polypeptide prepared according to the present invention is purified using methods generally known in the art, such as affinity purification and separations based on size, charge, solubility and other properties of the protein. When the protein is produced in cultured mammalian cells, it is preferred to culture the cells in a serum-free culture medium in order to limit the amount of contaminating protein. The medium is harvested and fractionated. Preferred methods of fractionation include affinity chromatography, Q-Fast Flow Sepharose, MonoQ resin, FPLC, phenyl Sepharose, hydroxyapatite, Mono S and/or S-Sepharose.

Molecules of the present invention can be used to identify and isolate receptors for zins3. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

Antibodies to zins3 proteins and peptides may be used for affinity purification, for diagnostic assays, for determining circulating levels of zins3 polypeptides and as antagonists to block zins3 binding and signal transduction in vivo and in vitro.

The activity of molecules of the present invention can be measureing using a variety of assays that measure cell proliferation, differentiation or regulation of metabolic processes. Of particular interest, are changes in proliferation, differentiation and motility of cells found in the reproductive, gastrointestinal (including the colon) system and pituitary cells. Proliferation and differentiation can be measured using cultured cells or in vivo by administering molecules of the claimed invention to the appropriate animal model. Assays measuring cell proliferation or differentiation are well known in the art. For example, assays measuring proliferation include such assays as chemosensitivity to neutral red dye (Cavanaugh et al., *Investigational New Drugs* 8:347–354, 1990, incorporated herein by reference), incorporation of radiolabelled nucleotides (Cook et al., *Analytical Biochem.* 179:1–7, 1989, incorporated herein by reference), incorporation of 5-bromo-2'-deoxyuridine (BrdU) in the DNA of proliferating cells (Porstmann et al., *J. Immunol. Methods* 82:169–179, 1985, incorporated herein by reference), and use of tetrazolium salts (Mosmann, *J. Immunol. Methods* 65:55–63, 1983; Alley et al., *Cancer Res.* 48:589–601, 1988; Marshall et al., *Growth Reg.* 5:69–84, 1995; and Scudiero et al., *Cancer Res.* 48:4827–4833, 1988; all incorporated herein by reference). Assays measuring differentiation include, for example, measuring cell-surface markers associated with stage-specific expression of a tissue, enzymatic activity, functional activity or morphological changes (Watt, *FASEB,* 5:281–284, 1991; Francis, *Differentiation* 57:63–75, 1994; Raes, *Adv. Anim. Cell Biol. Technol. Bioprocesses,* 161–171, 1989; all incorporated herein by reference).

An exemplary in vivo assay is when mammalian transfected (or co-transfected) expression host cells are embedded in an alginate environment and injected (implanted) into recipient animals. Alginate-poly-L-lysine microencapsulation, permselective membrane encapsulation and diffusion chambers have been described as a means to entrap transfected mammalian cells or primary mammalian cells. These types of non-immunogenic "encapsulations" or microenvironments permit the transfer of nutrients into the microenvironment, and also permit the diffusion of proteins and other macromolecules secreted or released by the captured cells across the environmental barrier to the recipient animal. Most importantly, the capsules or microenvironments mask and shield the foreign, embedded cells from the recipient animal's immune response. Such microenvironments can extend the life of the injected cells from a few hours or days (naked cells) to several weeks (embedded cells).

Alginate threads provide a simple and quick means for generating embedded cells. The materials needed to generate the alginate threads are readily available and relatively inexpensive. Once made, the alginate threads are relatively strong and durable, both in vitro and, based on data obtained using the threads, in vivo. The alginate threads are easily manipulable and the methodology is scalable for preparation of numerous threads. In an exemplary procedure, 3% alginate is prepared in sterile $H_2O$, and sterile filtered. Just prior to preparation of alginate threads, the alginate solution is again filtered. An approximately 50% cell suspension (containing about $5 \times 10^5$ to about $5 \times 10^7$ cells/ml) is mixed with the 3% alginate solution. One ml of the alginate/cell suspension is extruded into a 100 mM sterile filtered $CaCl_2$ solution over a time period of ~15 min, forming a "thread". The extruded thread is then transferred into a solution of 50 mM $CaCl_2$, and then into a solution of 25 mM $CaCl_2$. The thread is then rinsed with deionized water before coating the thread by incubating in a 0.01% solution of poly-L-lysine. Finally, the thread is rinsed with Lactated Ringer's Solution and drawn from solution into a syringe barrel (without needle attached). A large bore needle is then attached to the syringe, and the thread is intraperitoneally injected into a recipient in a minimal volume of the Lactated Ringer's Solution.

An alternative in vivo approach for assaying proteins of the present invention involves viral delivery systems. Exemplary viruses for this purpose include adenovirus, herpesvirus, vaccinia virus and adeno-associated virus (AAV). Adenovirus, a double-stranded DNA virus, is currently the best studied gene transfer vector for delivery of heterologous nucleic acid (for a review, see T. C. Becker et al., *Meth. Cell Biol.* 43:161–89, 1994; and J. T. Douglas and D. T. Curiel, *Science & Medicine* 4:44–53, 1997, each incorporated herein by reference). The adenovirus system offers several advantages: adenovirus can (i) accommodate relatively large DNA inserts; (ii) be grown to high-titer; (iii) infect a broad range of mammalian cell types; and (iv) be used with a large number of available vectors containing different promoters. Also, because adenoviruses are stable in the bloodstream, they can be administered by intravenous injection. Some disadvantages (especially for gene therapy) associated with adenovirus gene delivery include: (i) very low efficiency integration into the host genome; (ii) existence in primarily episomal form; and (iii) the host immune response to the administered virus, precluding readministration of the adenoviral vector.

By deleting portions of the adenovirus genome, larger inserts (up to 7 kb) of heterologous DNA can be accommodated. These inserts may be incorporated into the viral DNA by direct ligation or by homologous recombination with a co-transfected plasmid. In an exemplary system, the essential E1 gene has been deleted from the viral vector, and the virus will not replicate unless the E1 gene is provided by the host cell (i.e., the human 293 cell line). When intravenously administered to intact animals, adenovirus primarily targets the liver. If the adenoviral delivery system has an E1 gene deletion, the virus cannot replicate in the host cells. However, the host's tissue (i.e., liver) will express and process (and, if a signal sequence is present, secrete) the heterologous protein. Secreted proteins will enter the circulation in the highly vascularized liver, and effects on the infected animal can be determined.

The adenovirus system can also be used for protein production in vitro. By culturing adenovirus-infected non-293 cells under conditions where the cells are not rapidly dividing, the cells can produce proteins for extended periods of time. For instance, BHK cells are grown to confluence in cell factories, then exposed to the adenoviral vector encoding the secreted protein of interest. The cells are then grown under serum-free conditions, which allows infected cells to survive for several weeks without significant cell division. Alternatively, adenovirus vector infected 293S cells can be grown in suspension culture at relatively high cell density to produce significant amounts of protein (see A. Garnier et al., *Cytotechnol.* 15:145–55, 1994, incorporated herein by reference). With either protocol, an expressed, secreted heterologous protein can be repeatedly isolated from the cell culture supernatant. Within the infected 293S cell production protocol, non-secreted proteins may also be effectively obtained.

Assays can be used to measure other cellular responses, that include, chemotaxis, adhesion, changes in ion channel influx, regulation of second messenger levels and neurotransmitter release. Such assays are well known in the art. See, for example, in "Basic & Clinical Endocrinology Ser., Vol. Vol. 3," *Cytochemical Bioassays: Techniques & Applications,* Chayen; Chayen, Bitensky, eds., Dekker, N.Y., 1983.

In view of the tissue distribution observed for this Zins3, agonists (including the natural ligand) and antagonists have enormous potential in both in vitro and in vivo applications. Compounds identified as Zins3 agonists are useful for stimulating proliferation and/or differentiation of cells in culture. For example, agonist compounds are useful as components of defined cell culture media, and may be used alone or in combination with other cytokines and hormones to replace serum that is commonly used in cell culture. Agonists are thus useful in specifically promoting the growth and/or development of cells derived from aortic or ovarian tissues or endothelial cells in culture.

Antagonists will be useful for inhibiting expression of specialized cell functions, such as production of extracellular components and inhibition of cell proliferation. Genes encoding polypeptides having potential Zins3 polypeptide binding domains can be obtained by screening random peptide libraries displayed on phage (phage display) or on bacteria, such as *E. coli.* Nucleotide sequences encoding the polypeptides can be obtained in a number of ways, such as through random mutagenesis and random polynucleotide synthesis. These random peptide display libraries can be used to screen for peptides which interact with a known target which can be a protein or polypeptide, such as a ligand or receptor, a biological or synthetic macromolecule, or organic or inorganic substances. Techniques for creating and screening such random peptide display libraries are known in the art (Ladner et al., U.S. Pat. No. :5,223,409; Ladner et al., U.S. Pat. No. :4,946,778; Ladner et al., U.S. Pat. No.:5,403,484 and Ladner et al., U.S. Pat. No. :5,571,698) and random peptide display libraries and kits for screening such libraries are available commercially, for instance from Clontech (Palo Alto, Calif.), Invitrogen Inc. (San Diego, Calif.), New England Biolabs, Inc. (Beverly, Mass.) and Pharmacia LKB Biotechnology Inc. (Piscataway, N.J.). Random peptide display libraries can be screened using the Zins3 sequences disclosed herein to identify proteins which bind to Zins3. These "binding proteins" which interact with Zins3 polypeptides may be used for tagging cells; for isolating homolog polypeptides by affinity purification; they can be directly or indirectly conjugated to drugs, toxins, radionuclides and the like. These binding proteins can also be used in analytical methods such as for screening expression libraries and neutralizing activity. The binding proteins can also be used for diagnostic assays for determining circulating levels of polypeptides; for detecting or quantitating soluble polypeptides as marker of underlying pathology or disease. These binding proteins can also act as Zins3 "antagonists" to block Zins3 binding and signal transduction in vitro and in vivo. These anti-Zins3 binding proteins would be useful for inhibiting expression of genes which result in proliferation, differentiation, motility, secretion or reproductive regulation. Such anti-Zins3 binding proteins can be used for treatment in diseases associated with extracellular matrix and vessels, such as arteriosclerosis, endometriosis, breast cancer, ovarian cancers, and lung fibrotic diseases, alone or combination with other therapies.

An assay system that uses an antibody, one member of a complement/ anti-complement pair or a binding fragment thereof, and a commercially available biosensor instrument (BIAcore™, Pharmacia Biosensor, Piscataway, N.J.) may be advantageously employed. Such antibody, member of a complement/anti-complement pair or fragment is immobilized onto the surface of a receptor chip. Use of this instrument is disclosed by Karlsson, *J. Immunol. Methods* 145:229–40, 1991 and Cunningham and Wells, *J. Mol. Biol.* 234:554–63, 1993. An antibody, member of a complement/ anti-complement pair or fragment is covalently attached, using amine or sulfhydryl chemistry, to dextran fibers that are attached to gold film within the flow cell. A test sample is passed through the cell. If an epitope, or opposite member of the complement/anti-complement pair is present in the sample, it will bind to the immobilized receptor, antibody or member, respectively, causing a change in the refractive index of the medium, which is detected as a change in surface plasmon resonance of the gold film. This system allows the determination of on- and off-rates, from which binding affinity can be calculated, and assessment of stoichiometry of binding.

Zins3 polypeptides can also be used to prepare antibodies that specifically bind to Zins3 epitopes, peptides or polypeptides. Methods for preparing polyclonal and monoclonal antibodies are well known in the art (see, for example, Sambrook et al., *Molecular Cloning: A Laboratory Manual,* Second Edition, Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which are incorporated herein by reference). As would be evident to one of ordinary skill in the art, polyclonal antibodies can be generated from a variety of warm-blooded animals, such as horses, cows, goats, sheep, dogs, chickens, rabbits, guinea pigs, mice, and rats.

The immunogenicity of a Zins3 polypeptide may be increased through the use of an adjuvant, such as alum (aluminum hydroxide) or Freund's complete or incomplete adjuvant. Polypeptides useful for immunization also include fusion polypeptides, such as fusions of Zins3 or a portion thereof with an immunoglobulin polypeptide or with maltose binding protein. The polypeptide immunogen may be a full-length molecule or a portion thereof. If the polypeptide portion is "hapten-like", such portion may be advantageously joined or linked to a macromolecular carrier (such as keyhole limpet hemocyanin (KLH), bovine serum albumin (BSA) or tetanus toxoid) for immunization.

As used herein, the term "antibodies" includes polyclonal antibodies, affinity-purified polyclonal antibodies, monoclonal antibodies, and antigen-binding fragments, such as F(ab')$_2$ and Fab proteolytic fragments. Genetically engineered intact antibodies or fragments, such as chimeric antibodies, Fv fragments, single chain antibodies and the like, as well as synthetic antigen-binding peptides and polypeptides, are also included. Non-human antibodies may be humanized by grafting only non-human CDRs onto human framework and constant regions, or by incorporating the entire non-human variable domains (optionally "cloaking" them with a human-like surface by replacement of exposed residues, wherein the result is a "veneered" antibody). In some instances, humanized antibodies may retain non-human residues within the human variable region framework domains to enhance proper binding characteristics. Through humanizing antibodies, biological half-life may be increased, and the potential for adverse immune reactions upon administration to humans is reduced. Alternative techniques for generating or selecting antibodies useful herein include in vitro exposure of lymphocytes to Zins3 protein or peptide, and selection of antibody display libraries in phage or similar vectors (for instance, through use of immobilized or labeled Zins3 protein or peptide).

Antibodies are defined to be specifically binding if: 1) they exhibit a threshold level of binding activity, and/or 2) they do not significantly cross-react with related polypeptide molecules. First, antibodies herein specifically bind if they bind to a Zins3 polypeptide, peptide or epitope with a binding affinity (Ka) of $10^6$ mol$^{-1}$ or greater, preferably $10^7$ mol$^{-1}$ or greater, more preferably $10^8$ mol$^{-1}$ or greater, and most preferably $10^9$ mol$^{-1}$ or greater. The binding affinity of an antibody can be readily determined by one of ordinary skill in the art, for example, by Scatchard analysis (G. Scatchard, *Ann. N.Y. Acad. Sci.* 51: 660–72, 1949).

Second, antibodies specifically bind if they do not significantly cross-react with related polypeptides. Antibodies do not significantly cross-react with related polypeptide molecules, for example, if they detect human Zins3 polypeptide, but not known related polypeptides using a standard Western blot analysis (Ausubel et al., ibid.). Examples of known related polypeptides are orthologs, that is, proteins from the same species that are members of a protein family, such as other known human insulin homologs (e.g., human Leydig Factor or human INSL4 (EPIL)). Moreover, antibodies may be "screened against" known related polypeptides to isolate a population that specifically binds to the inventive polypeptides. For example, antibodies raised to human Zins3 polypeptide are adsorbed with related polypeptides adhered to an insoluble matrix; antibodies specific to human Zins3 polypeptide will flow through the matrix under the proper buffer conditions. Such screening allows isolation of polyclonal and monoclonal antibodies non-crossreactive to closely related polypeptides (see, Antibodies: A Laboratory Manual, Harlow and Lane (eds.), Cold Spring Harbor Laboratory Press, 1988; Current Protocols in Immunology, Cooligan et al. (eds.), National Institutes of Health, John Wiley and Sons, Inc., 1995). Screening and isolation of specific antibodies is well known in the art (see, Fundamental Immunology, Paul (ed.), Raven Press, 1993; Getzoff et al., *Adv. Immunol.* 43:1–98, 1988; Monoclonal Antibodies: Principles and Practice, Goding, J. W. (eds.), Academic Press Ltd., 1996; Benjamin et al., *Ann. Rev. Immunol.* 2:67–101, 1984).

A variety of assays known to those skilled in the art can be utilized to detect antibodies which specifically bind to Zins3 proteins or peptides. Exemplary assays are described in detail in *Antibodies: A Laboratory Manual*, Harlow and Lane (Eds.), Cold Spring Harbor Laboratory Press, 1988. Representative examples of such assays include: concurrent immunoelectrophoresis, radioimmunoassay, radioimmunoprecipitation, enzyme-linked immunosorbent assay (ELISA), dot blot or Western blot assay, inhibition or competition assay, and sandwich assay. In addition, antibodies can be screened for binding to wild-type versus mutant Zins3 protein or peptide.

Antibodies to Zins3 may be used for tagging cells that express Zins3; for isolating Zins3 by affinity purification; for diagnostic assays for determining circulating levels of Zins3 polypeptides; for detecting or quantitating soluble Zins3 as marker of underlying pathology or disease; in analytical methods employing FACS; for screening expression libraries; for generating anti-idiotypic antibodies; and as neutralizing antibodies or as antagonists to block Zins3 in vitro and in vivo. In particular, antibodies will be useful for diagnostics, due to the association of proteins of the present invention with placenta and colon pathology, and labeled proteins will be useful in the diagnosis of diseases such as reproductive disorders associated with the placenta and uterus and gastrointestinal disease.

Antibodies or polypeptides herein may also be directly or indirectly conjugated to drugs, toxins, radionuclides and the like, and these conjugates used for in vivo diagnostic or therapeutic applications. For instance, polypeptides or antibodies of the present invention may used to identify or treat tissues or organs that express a corresponding anti-complementary molecule (receptor or antigen, respectively, for instance). More specifically, Zins3 polypeptides or anti-Zins3 antibodies, or bioactive fragments or portions thereof, can be coupled to detectable or cytotoxic molecules and delivered to a mammal having cells, tissues or organs that express the anti-complementary molecule. For example, for use of the antibodies and polypeptides, labeled for detection by imaging technologies, will be useful for diagnosing diseases associated with extracellular matrix and vessels, such as, arteriosclerosis, endometriosis, breast cancer, ovarian cancers, and lung fibrotic diseases.

Suitable detectable molecules may be directly or indirectly attached to the polypeptide or antibody, and include radionuclides, enzymes, substrates, cofactors, inhibitors, fluorescent markers, chemiluminescent markers, magnetic particles and the like. Suitable cytotoxic molecules may be directly or indirectly attached to the polypeptide or antibody, and include bacterial or plant toxins (for instance, diphtheria toxin, Pseudomonas exotoxin, ricin, abrin and the like), as well as therapeutic radionuclides, such as iodine-131, rhenium-188 or yttrium-90 (either directly attached to the polypeptide or antibody, or indirectly attached through means of a chelating moiety, for instance). Polypeptides or antibodies may also be conjugated to cytotoxic drugs, such as adriamycin. For indirect attachment of a detectable or cytotoxic molecule, the detectable or cytotoxic molecule may be conjugated with a member of a complementary/anticomplementary pair, where the other member is bound to the polypeptide or antibody portion. For these purposes, biotin/streptavidin is an exemplary complementary/anticomplementary pair.

In another embodiment, polypeptide-toxin fusion proteins or antibody/fragment-toxin fusion proteins may be used for targeted cell or tissue inhibition or ablation (for instance, to treat diseases caused by inappropriate growth of cells or tissues).

Such molecule fusion proteins thus represent a generic targeting vehicle for cell/tissue-specific delivery of generic anti-complementary-detectable/cytotoxic molecule conjugates.

The bioactive polypeptide or antibody conjugates described herein can be delivered intravenously, intraarterially or intraductally, or may be introduced locally at the intended site of action.

Molecules of the present invention can be used to identify and isolate receptors involved in growth and differentiation of Zins3 responsive cells. For example, proteins and peptides of the present invention can be immobilized on a column and membrane preparations run over the column (*Immobilized Affinity Ligand Techniques,* Hermanson et al., eds., Academic Press, San Diego, Calif., 1992, pp.195–202). Proteins and peptides can also be radiolabeled (*Methods in Enzymol.,* vol. 182, "Guide to Protein Purification", M. Deutscher, ed., Acad. Press, San Diego, 1990, 721–737) or photoaffinity labeled (Brunner et al., *Ann. Rev. Biochem.* 62:483–514, 1993 and Fedan et al., *Biochem. Pharmacol.* 33:1167–1180, 1984) and specific cell-surface proteins can be identified.

The molecules of the present invention will be useful for regulating the growth and/or differentiation of Zins3 responsive cells. The polypeptides, nucleic acid and/or antibodies of the present invention may be used in treatment of disorders associated with unregulated growth in Zins3-responsive tissues. In particular, the molecules of the present may used to produce antagonists to treat or prevent development of pathological conditions in tissues as placenta, uterus, and colon. Certain diseases such as preclampsia, premature labor and Crohn's disease may be amenable to such diagnosis, treatment or prevention.

If a mammal has a mutated or absent Zins3 gene, the Zins3 gene can be introduced into the cells of the mammal. In one embodiment, a gene encoding a Zins3 polypeptide is introduced in vivo in a viral vector. Such vectors include an attenuated or defective DNA virus, such as, but not limited to, herpes simplex virus (HSV), papillomavirus, Epstein Barr virus (EBV), adenovirus, adeno-associated virus (AAV), and the like. Defective viruses, which entirely or almost entirely lack viral genes, are preferred. A defective virus is not infective after introduction into a cell. Use of defective viral vectors allows for administration to cells in a specific, localized area, without concern that the vector can infect other cells. Examples of particular vectors include, but are not limited to, a defective herpes simplex virus 1 (HSV1) vector (Kaplitt et al., *Molec. Cell. Neurosci.* 2:320–30, 1991); an attenuated adenovirus vector, such as the vector described by Stratford-Perricaudet et al., *J. Clin. Invest.* 90:626–30, 1992; and a defective adeno-associated virus vector (Samulski et al., *J. Virol.* 61:3096–101, 1987; Samulski et al., *J. Virol.* 63:3822–28, 1989). Recently, adenoviral/retroviral chimeric vectors have been developed to deliver retroviral packaging plasmids to target cells, converting them to retroviral packaging cells and allowing the release of high concentrations of retrovirus, to infect cells (Feng et al., *Nature Biotech.* 15:866–870, 1997).

In another embodiment, the Zins3 gene can be introduced in a retroviral vector, e.g., as described in Anderson et al., U.S. Pat. No. 5,399,346; Mann et al. *Cell* 33:153, 1983; Temin et al., U.S. Pat. No. 4,650,764; Temin et al., U.S. Pat. No. 4,980,289; Markowitz et al., *J. Virol.* 62:1120, 1988; Temin et al., U.S. Pat. No. 5,124,263; International Patent Publication No. WO 95/07358, published Mar. 16, 1995 by Dougherty et al.; and Kuo et al., *Blood* 82:845–852, 1993. Alternatively, the vector can be introduced by lipofection in vivo using liposomes. Synthetic cationic lipids can be used to prepare liposomes for in vivo transfection of a gene encoding a marker (Felgner et al., *Proc. Natl. Acad. Sci. USA* 84:7413–17, 1987; Mackey et al., *Proc. Natl. Acad. Sci. USA* 85:8027–31, 1988). The use of lipofection to introduce exogenous genes into specific organs in vivo has certain practical advantages. Molecular targeting of liposomes to specific cells represents one area of benefit. More particularly, directing transfection to particular cells represents one area of benefit. For instance, directing transfection to particular cell types would be particularly advantageous in a tissue with cellular heterogeneity, such as the pancreas, liver, kidney, and brain. Lipids may be chemically coupled to other molecules for the purpose of targeting. Targeted peptides (e.g., hormones or neurotransmitters), proteins such as antibodies, or non-peptide molecules could be coupled to liposomes chemically.

It is possible to remove the target cells from the body; to introduce the vector as a naked DNA plasmid; and then to re-implant the transformed cells into the body. Naked DNA vectors for gene therapy can be introduced into the desired host cells by methods known in the art, e.g., transfection, electroporation, microinjection, transduction, cell fusion, DEAE dextran, calcium phosphate precipitation, use of a gene gun or use of a DNA vector transporter. See, e.g., Wu et al., *J. Biol. Chem.* 267:963–67, 1992; Wu et al., *J. Biol. Chem.* 263:14621–24, 1988.

Another aspect of the present invention involves antisense polynucleotide compositions that are complementary to a segment of the polynucleotides set forth in SEQ ID NO: 1. Such synthetic antisense oligonucleotides are designed to bind to mRNA encoding Zins3 polypeptides and to inhibit translation of such mRNA. Such antisense oligonucleotides are used to inhibit expression of Zins3 polypeptide-encoding genes in cell culture or in a subject.

The present invention also provides reagents which will find use in diagnostic applications. For example, the Zins3 gene, a probe comprising Zins3 DNA or RNA or a subsequence thereof can be used to determine if the Zins3 gene is present on chromosome 12 or if a mutation has occurred. Detectable chromosomal aberrations at the Zins3 gene locus include, but are not limited to, aneuploidy, gene copy number changes, insertions, deletions, restriction site changes and rearrangements. Such aberrations can be detected using polynucleotides of the present invention by employing molecular genetic techniques, such as restriction fragment length polymorphism (RFLP) analysis, short tandem repeat (STR) analysis employing PCR techniques, and other genetic linkage analysis techniques known in the art (Sambrook et al., ibid.; Ausubel et. al., ibid.; A. J. Marian, *Chest* 108:255–65, 1995).

Transgenic mice, engineered to express the Zins3 gene, and mice that exhibit a complete absence of Zins3 gene function, referred to as "knockout mice" (Snouwaert et al., *Science* 257:1083, 1992), may also be generated (Lowell et al., *Nature* 366:740–42, 1993). These mice may be employed to study the Zins3 gene and the protein encoded thereby in an in vivo system.

Radiation hybrid mapping is a somatic cell genetic technique developed for constructing high-resolution, contiguous maps of mammalian chromosomes (Cox et al., *Science* 250:245–50, 1990). Partial or full knowledge of a gene's sequence allows one to design PCR primers suitable for use with chromosomal radiation hybrid mapping panels. Commercially available radiation hybrid mapping panels which cover the entire human genome, such as the Stanford G3 RH Panel and the GeneBridge 4 RH Panel (Research Genetics, Inc., Huntsville, Ala.), are available. These panels enable rapid, PCR-based chromosomal localizations and ordering of genes, sequence-tagged sites (STSs), and other nonpolymorphic and polymorphic markers within a region of interest. This includes establishing directly proportional physical distances between newly discovered genes of interest and previously mapped markers. The precise knowledge of a gene's position can be useful for a number of purposes, including: 1) determining if a sequence is part of an existing contig and obtaining additional surrounding genetic sequences in various forms, such as YACs, BACs or cDNA clones; 2) providing a possible candidate gene for an inheritable disease which shows linkage to the same chromosomal region; and 3) cross-referencing model organisms, such as mouse, which may aid in determining what function a particular gene might have.

The gene corresponding to the cDNA of the present invention has been mapped to chromosome 12q24.33. This region has recently been identified as possible loci for a cluster of genes involved in diabetes (Mahtani et al., *Nature Genetics*, 14:90–94, 1996). Chromosome 12q is the location of MODY3, a gene associated with a rare, dominant, early-onset form of diabetes (Vaxillaire et al., *Nature Genetics*, 9:418–423, 1995). Therefore, polynucleotides of the present invention may useful as specific markers for mapping this area of the chromosome, and ultimately provide sequence information that correlates to genes to disease. Chromosomal mapping techniques are well known to those skilled in the art, and include such methods as PCR mapping of somatic cell hybrids (Drwinga et al., *Genomics* 16:311, 1993 and Dubois et al., *Genomics* 16:315, 1993), radiation hybrid mapping (Cox et al., *Science* 250: 245–250, 1990 and Boehnke et al., *Am. J. Hum. Genet.* 49:1174–1188, 1991) and fluorescence in situ hybridization (FISH; Verma et al., *Human Chromosomes: A Manual of Basic Techniques*, Pergamon Press, NY, 1988).

For pharmaceutical use, the proteins of the present invention are formulated for parenteral, particularly intravenous or subcutaneous, delivery according to conventional methods. Intravenous administration will be by bolus injection or infusion over a typical period of one to several hours. In general, pharmaceutical formulations will include a zins3 protein in combination with a pharmaceutically acceptable vehicle, such as saline, buffered saline, 5% dextrose in water or the like. Formulations may further include one or more excipients, preservatives, solubilizers, buffering agents, albumin to prevent protein loss on vial surfaces, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Determination of dose is within the level of ordinary skill in the art. The proteins may be administered for acute treatment, over one week or less, often over a period of one to three days or may be used in chronic treatment, over several months or years.

The invention is further illustrated by the following non-limiting examples.

EXAMPLES

Example 1

Scanning of a cDNA database for sequences structurally homologous to insulin revealed an expressed sequence tag (EST) from a human colon cDNA library that is homologous to relaxin. This EST encoded a secretory signal sequence followed by the insulin, family B chain motif. Analysis of the sequence revealed a putative amphipathic helix, providing additional confirmation of an insulin B chain homology.

Confirmation of the EST sequence was made by sequence analyses of the cDNA from which the EST originated. This cDNA was contained in a plasmid designated pSL8319, and the analyses revealed that the cDNA encompassed the entire coding region of the DNA encoding zins3. The cDNA insert was isolated from pSL8319 by digesting the plasmid with Xba I and Sal I, utilizing cloning sites in the polylinker. These same cloning sites were utilized for ligation of the excised cDNA into a mammalian expression vector designated pHZ-200 and resulted in a plasmid designated pHZ200ZINS3.

pHZ-200 is the same as pHZ-1 with the exception that the dihydrofolate reductase sequence was substituted for the neomycin resistance gene. Plasmid pHZ-1 is an expression vector that may be used to express protein in mammalian cells or in a frog oocyte translation system from mRNAs that have been transcribed in vitro. The pHZ-1 expression unit comprises the mouse metallothionein-1 promoter, the bacteriophage T7 promoter flanked by multiple cloning banks containing unique restriction sites for insertion of coding sequences, the human growth hormone terminator and the bacteriophage T7 terminator. In addition, pHZ-1 contains an *E. coli* origin of replication; a bacterial beta lactamase gene; a mammalian selectable marker expression unit comprising the SV40 promoter and origin, a neomycin resistance gene and the SV40 transcription terminator.

Example 2

Northerns were performed using Human Multiple Tissue Blots from Clontech (Palo Alto, Calif.). The probe was approximately 300 bp PCR product amplified from plasmid pSL8319 using oligonucleotide primers ZC11,142 (SEQ ID NO: 3) and ZC11,140 (SEQ ID NO: 4). The probe was amplified in a polymerase chain reaction as follows: 25 cycles of 94° C. for 20 seconds, 55° C. for 30 seconds and 72° C. for 1 minute, followed by 1 cycle at 72° C. for 10 minutes and 4° C. incubation period. The resulting DNA fragment was electrophoresed on a 1% agarose gel, the fragment was purifed using the QIAQUICK (Qiagen, Chatsworth, Calif.), and then radioactively labeled using a random priming MULTIPRIME DNA labeling system (Amersham, Arlington Heights, Ill.), according to the manufacturer's specifications. The probe was purified using a NUCTRAP push colums (Stratagene, La Jolla, Calif.). EXPRESSHYB (Clontech) solution was used for prehybridization and as a hybridizing solution for the Northern blots. Hybridization took place at 68° C., and the blots were washed 4 times in 2×SSC and 0.05% SDS at RT, followed by 2 washes in 0.1×SSC and 0.1% SDS at 50° C. A weak transcript was observed in placental tissue at approximately 7 kb, after a 1 week exposure. A RNA Master Dot Blot (Clontech) that contained RNAs from various tissues that were normalized to 6 housekeeping genes was also probed with 300 bp PCR product probe. The blot was prehybridized and then hybridized overnight with 106 cpm/ml of the probe, overnight, at 65° C., according to the manufacturer's specifications. The blot was washed 4 times with 2×SSC and 0.05% SDS at 65° C., followed by 2 washes in 0.1×SSC and 0.1% SDS at 55° C. After a 48 hour exposure, highest expression was seen in the uterus, with weaker signals in kidney and placenta.

Example 3

Zins3 was mapped to chromosome 12 using the commercially available version of the Whitehead Institute/MIT Center for Genome Research's "GeneBridge 4 Radiation Hybrid Panel" (Research Genetics, Inc., Huntsville, Ala.). The GeneBridge 4 Radiation Hybrid Panel contains DNAs that can be utilized for PCR amplication from each of 93 radiation hybrid clones, plus two control DNAs (the HFL donor and the A23 recipient). A publicly available world wide web (WWW) server (http://www-genome.wi.mit.edu/cgi-bin/contig/rhmapper.pl) allows mapping relative to the Whitehead Institute/MIT Center for Genome Research's radiation hybrid map of the human genome (the "WICGR" radiation hybrid map) which was constructed with the GeneBridge 4 Radiation Hybrid Panel.

For the mapping of zins3 with the "GeneBridge 4 RH Panel", 25 µl reactions were set up in a 96-well microtiter plate (Stratagene, La Jolla, Calif.) and used in a "RoboCycler Gradient 96" thermal cycler (Stratagene) for PCR amplification. Each of the 95 PCR reactions consisted of 2.5 µl 50× "Advantage KlenTaq Polymerase Mix" (CLONTECH Laboratories, Inc.), 2 µl dNTPs mix (2.5 mM each, PERKIN-ELMER, Foster City, Calif.), 1.25 µl sense primer, ZC 11,142, (SEQ ID NO: 3), 1.25 µl antisense primer, ZC 11,140 (SEQ ID NO: 4), 2.5 µl "RediLoad" (Research Genetics, Inc., Huntsville, Ala.), 0.5 µl "Advantage KlenTaq Polymerase Mix" (Clontech Laboratories, Inc.), 25 ng of DNA from an individual hybrid clone or control and ddH2O for a total volume of 25 µl. The reactions were overlaid with an equal amount of mineral oil and sealed. The PCR cycler conditions were as follows: an initial 1 cycle 4 minutes at 94° C., 35 cycles of a 1 minute at 94° C., 1.5 minute annealing at 57° C. and 1.5 minute extension at 72° C., followed by a final 1 cycle extension of 7 minutes at 72° C. The reactions were separated by electrophoresis on a 3% NuSieve GTG agarose gel (FMC Bioproducts, Rockland, Me.).

The results showed that zins3 maps 617.10 cR from the top of the human chromosome 12 linkage group on the WICGR radiation hybrid map. Its nearest proximal marker was D12S367 and its nearest distal maker was WI-12272. It is within 270 kb of SGC31722 which also maps at 617.10 cR. The use of other surrounding WICGR map markers also helped position zins3 in the 12q24.35 region on the CHLC chromosome 12 version v8c7 integrated marker map (The Cooperative Human Linkage Center, WWW server-http://www.chlc.org/ChlcIntegratedMaps.html). This data indicates that zins3 is in a chromosomal region known to be linked to: 1.) MODY3 (Menzel et al., Diabetes 44:1408–1435, 1995), 2.) a gene for type-2 diabetes associated with an insulin secretion defect (Mahtani et al., Nature Genet. 14:90–94, 1996) and 3.) diabetes complications in NIDDM kindreds (Velho et al., Diabetes Care 19:915–919, 1996).

Example 4

The mouse paralog of Zins3 was cloned using ESTs identified in a mouse cDNA database. A clone corresponding to the ESTs was sequenced by was prematurely terminated at the C-terminus, missing approximately 20 amino acids.

An EST with additional 3' sequence was identified and the corresponding cDNA clone was sequenced and found to contain the full length mouse zins3.

An EcoRl-Pst fragment (polynucleotide 1 to polynucleotide 422 of SEQ ID NO: 5) was used as a probe for a mouse embryonic northern blot (Clontech). The 330 bp fragment was electrophoresed on a 1% agarose gel (GIBCO-BRL, Gaithersburg, Md.), and gel purified using QIAEXII resin (Qiagen Inc., Chatsworth, Calif.), according to manufacturer's instructions. The resulting DNA fragment was labelled with $^{32}$P dCTP using a MULTIPRIME random labeling kit (Amsersham), and labeled DNA fragment was separated from excess label by a NUCTRAP push column (Stratagene), both procedures done according to the manufacturers' instructions. The northern blot was prehybrized about 3 hours at 60° C. in EXPRESSHYB solution (Clontetch). After prehybridization, the probe was added at a concentration of 2×10$^6$ cpm/ml with a change of EXPRESSHYB. The blots were incubated overnight at 60° C. The next day, the blots were washed several times at room temp in 2×SSC, 0.1% SDS, followed by a wash in 0.1×SSC, 0.1% SDS at 50° C., and exposed for two days to X-ray film. An approximately 1 kb transcript was seen exclusively in the day 17, but not in days 7, 11, and 15, mouse embryonic lane of the northern, suggesting that mouse Zins3 is expressed in developmentally regulated fashion.

Example 5

Antibodies for Zins3 were produced, using standard techniques known in the art and described previously, by immunizing guinea pigs, rabbits and chickens with peptides either to the A chain of Zins3 (Zins3-A) SVMSRQDLQTL-CCTDGCSMTDSALC (SEQ ID NO: 2 amino acid residue 110 to residue 135) or Zins3 B chain (Zins3-B) EVRSKES-VRLCGLEYIRTVIYICASSRWRRH (SEQ ID NO: 2 amino acid residue 19 to residue 49). Peptides were conjugated through Cys residues using Maleimide-activated KLH (Pierce Chem. Co., Rockford, Ill.).

Table 5 is a description of the animals, immunization levels and antibody separations.

TABLE 5

| Peptide or Protein | animal | immunization level | antibody produced |
|---|---|---|---|
| ZINS3-A | G.P. | 200 ug/animal initial 100 ug/animal boost | affinity purified and IgG fractionated |
| | Rabbit | 150 ug/animal initial 75 ug/animal boost | affinity purified and IgG fractionated |
| | Chickens | 100 ug/animal initial 100 ug/animal boost | IgY fractionated |
| ZINS3-B | G.P. | 200 ug/animal initial 100 ug/animal boost | affinity purified and IgG fractionated |
| | Rabbit | 150 ug/animal initial 75 ug/animal boost | affinity purified and IgG fractionated |
| | Chickens | 100 ug/animal initial 100 ug/animal boost | IgY fractionated |

Example 6

A mammalian expression construct of human Zins3 was made containing an affinity tag, FLAG (DYKDDDDK, as shown in SEQ ID NO: 8) at the N-terminus. PCR primers were designed to allow the insertion of the Zins3 protein sequence into a mammalian expression vector (pZP9NF; as shown in FIG. 2) containing an in-frame N-terminal affinity tag. A 5' primer contained an upstream BamHI site inframe with the zin3 sequence, beginning at residue 19 (Glu) of SEQ ID NO: 2, was designed along with a 3' primer with a downstream XbaI site immediately after the amino acid residue 135 (cys) and an in-frame stop codon. This product was obtained by PCR amplification from the original clone, pSL8319 (as described in Example 1), as follows: One cycle at 94° C. for one min, 35 cycles at 94° C. for 30 sec, 35 cycles at 55° C. for 20 sec, 35 cycles at 72° C. for 30 sec and one cycle at 72° C. for 10 min. The resulting product was electrophoresed on a 2% agarose gel, excised and purified using a QIAQUICK gel extraction kit (Qiagen). For insertion into the vector, both vector (pZP9NF) and insert were digested using BamHI and Xba I. The zins3 product contains an internal BamHI site so the digestion resulted in two fragments of 107 bp (BamHI/BamHI) and 254 bp (BamHI/Xba I). The digested insert was electrophoresed on a 2% agarose gel and the resulting fragments purified using the QIAQUICK gel extraction kit (Qiagen).

The purified BamHI/Xba I Zins3 fragment was ligated into the cut pZP9NF vector under the following conditions. Approximately 20 ng of purified insert was added to 5 ng of cut vector along with 0.5 µl of 10 mM ATP, 1.0 µl of 100 mM DTT, 2 µl of 5×ligase buffer (Gibco BRL) and 1.0 µl of T4 DNA ligase. The reaction was incubated at room temperature for 5 hrs then 25 µL of electrocompetent DH10b cells (Gibco BRL) were mixed with 1 µl of the ligation reaction and transformed. The transformants were plated onto LB-Amp plates at various dilutions and incubated overnight. The resulting colonies were screened by PCR to identify those containing the Bam/Xba insert. Two positive colonies were selected (designated zins3/pZP9NF/Bam/Xba 1 and 2), and plasmid DNA prepared from each. The DNA was cut with BamHI, treated with calf alkaline phosphatase and the linearized product electrophoresed on a 2% agarose gel followed by purification using the QIAQUICK system. The previously purified BamHI/BamHI Zins3 fragment was then ligated into zins3/pZP9NF/Bam/Xba 1 and 2 as above. DH10b cells were transformed and plated as above. Resulting colonies were screened by PCR for presence of insert and correct orientation of the Bam/Bam fragment. Five clones were sequenced; and clone zins3NF/1.4 had the correct sequence, and was used for transfection of mammalian cells.

Example 7

Purification of Zins3, N-terminally flagged polypeptide (as described above) is done using conditioned media from BHK 570 cells (ATCC accession no.10314) that are co-transfected with prohormone convertase 3 (PC3). The conditioned medium is concentrated 20× with a 3K MW cut-off membrane. Once concentrated, the 20× media is passed over a M2 antibody column (Kodak, Rochester, N.Y.) The column is eluted with 0.2 mg/ml of Flag peptide in PBS.

The fractions from the Antibody column are pooled, and concentrated to 2 ml. The concentrated elutate is applied to a gel filtration column (HW-40s; Toso Haas, Montgomeryville, Pa.) in PBS, to remove the FLAG tag peptide from the Zins3. After gel filtration further analysis is performed by Commassie gel, western analysis and total protein assay.

Example 8

Immunohistochemistry was used to determine tissue distribution and cell expression of Zins3.

The following samples were prepared by placing in 10% NBF fix for overnight, with the cell block embedded in paraffin the next day.

1. BHK cells transfected with Zins3 plasmid (positive control)
2. Untransfected BHK 570 cells (ATCC accession no.10314) (negative control).
3. Mouse Embryo, Day 16, Hybrid-Ready Slides (Novagen, Inc. Madison, Wis.) 10 slides of paraffin sections.
4. Multi-tissue normalGridt control slides/human tissues (Biomeda, Foster City, Calif.) that contained the following tissues: Brain, Pituitary, Adrenal, Breast, Kidney, Heart, Stomach, Small intestine, Large intestine, Fetal liver, Liver, Skin, Pancreas, Lung, Tonsil, Ovary, Uterus, Placenta, Thyroid, and Spleen.

The samples were probed with the following reagents:

1. Goat blocking antibodies (ChemMate, Fisher Scientific Co., Pittsburg, Pa.) used first to block non-specific binding by the conjugated secondary antibody
2. Primary antibody: D4726 Guinea pig anti-Zins3-A at 1:50 dilution of 91 µg/ml concentration.
3. Zins3-A peptide (A-C) at a 10× dilution of a concentration of about 400 µg/ml in distilled water
4. Secondary antibody: Biotinylated goat anti-guinea pig IgG (Vector Laboratories, Burlingame, Calif.) at a 1:200 dilution of a concentration of 1.5 mg/ml (Mar. 12, 1997). The seconday antibody was diluted in buffer with 2% normal goat serum in PBS.
5. ChemMate peroxidase/DAB Staining Kit (Fisher Scientific) that included DAB, ABC, Hematoxylin counter stain.

Immunostaining Procedure was done as follows:
Removal of paraffin using:

1. Xylene 5 min.
2. Xylene 5 min.
3. Xylene 5 min.
4. 100% EtOH 2 min.
5. 100% EtOH 2 min.
6. 95% EtOH 2 min.
7. Water wash 1 min.
8. dH2O Followed by Steam Heat Induced Epitope Retrieval for 20 min., as recommened in manufacturer's manual.
Followed by TechMate 500 Autoimmune staining:

1. Goat antibody blocking for 10 min.
2. Primary antibody Guinea pig anti-zins3 for 25 min.
3. Secondary antibody for 25 min.
4. HP blocking for 5 min., three times
5. ABC for 25 min.
6. DAB for 5 min., three times
7. Hematoxylin for 1 min.

The samples were cleared using:

1. 95% EtOH 20 dips
2. 100% EtOH 20 dips
3. 100% EtOH 20 dips
4. Xylene 20 dips
5. Xylene 20 dips and mounted on cell mounts.
Results:
The guinea pig anti- zins3-A was specific for cells transfected with Zins3.

Mouse Embryo (day 16, 1:50 dilution of primary antibody) results demonstrated specific binding for epithelial cells of the salivary gland. Multi-Tissue Control Slides (1:50 dilution of primary antibody) were positive for anterior pituitary, zona glomerulosa in adrenal cortex, islet cells in the pancreas, in the proximal convoluted tubules of the kidney, and a few cells scattered along the epithelium of the large intestine.

The cell types expressing Zins-3 in the pancreas, pituitary gland, and colon can be determined by doing special histology and immunohistochemical stainings if that is essential or necessary.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

We claim:

1. An isolated polynucleotide molecule encoding a polypeptide wherein the polynucleotide molecule is selected from the group consisting of:
   (a) a polynucleotide molecule comprising a first nucleotide sequence as shown in SEQ ID NO: 1 from nucleotide 161 to nucleotide 199 and a second nucleotide sequence as shown in SEQ ID NO: 1 from nucleotide 437 to nucleotide 481;
   (b) a polynucleotide molecule comprising a first nucleotide sequence as shown in SEQ ID NO: 5 from nucleotide 136 to nucleotide 174 and a second nucleotide sequence as shown in SEQ ID NO: 5 from nucleotide 412 to nucleotide 456; and
   (c) a polynucleotide molecule comprising a first nucleotide sequence that encodes a polypeptide that is the amino acid sequence of SEQ ID NO: 2 from amino acid residue 29 (Cys) to amino acid residue 121 (Cys) and a second nucleotide sequence that encodes a polypeptide that is the amino acid sequence of SEQ ID NO: 2 from amino acid residue 121 (Cys) to amino acid residue 135 (Cys).

2. The isolated polynucleotide molecule of claim 1, wherein the molecule comprises a first nucleotide sequence as shown in SEQ ID NO: 1 from nucleotide 143 to nucleotide 214, and a second nucleotide sequence as shown in SEQ ID NO: 1 from nucleotide 419 to nucleotide 481.

3. The isolated polynucleotide molecule of claim 1, wherein the molecule comprises a first nucleotide sequence that encodes a polypeptide as shown in SEQ ID NO: 2 from amino acid residue 23 (Lys) to residue 46 (Trp), and second nucleotide sequence that encodes a polypeptide as shown in SEQ ID NO: 2 from amino acid residue 115 (Gln) to residue 135 (Cys).

4. An isolated polynucleotide molecule encoding a polypeptide wherein the polynucleotide molecule is selected from the group consisting of:
   (a) a polynucleotide molecule comprising a first nucleotide sequence as shown in SEQ ID NO: 1 from nucleotide 143 to nucleotide 220 and a second nucleotide sequence as shown in SEQ ID NO: 1 from nucleotide 419 to nucleotide 481;
   (b) a polynucleotide molecule comprising a first nucleotide sequence as shown in SEQ ID NO: 5 from nucleotide 118 to nucleotide 195 and a second nucleotide sequence as shown in SEQ ID NO: 5 from nucleotide 397 to nucleotide 456;
   (c) a polynucleotide molecule comprising a first nucleotide sequence that encodes a polypeptide that is the amino acid sequence of SEQ ID NO: 2 from amino acid residue 23 (Lys) to residue 48 (Arg) and a second nucleotide sequence that encodes a polypeptide that is the amino acid sequence of SEQ ID NO: 2 from amino acid residue 115 (Gln) to residue 135 (Cys); and
   (d) a polynucleotide molecule comprising a nucleotide sequence as shown in SEQ ID NO: 7 from nucleotide 67 to nucleotide 144 and from nucleotide 343 to nucleotide 405.

5. An isolated polynucleotide molecule encoding a polypeptide wherein the polynucleotide molecule is selected from the group consisting of:
   (a) a polynucleotide molecule comprising a nucleotide sequence as shown in SEQ ID NO: 1 from nucleotide 77 or nucleotide 143 to nucleotide 481;
   (b) a polynucleotide molecule comprising a nucleotide sequence as shown in SEQ ID NO: 5 from nucleotide 52 or nucleotide 118 to nucleotide 457;
   (c) a polynucleotide molecule comprising a nucleotide sequence that encodes a polypeptide that is the amino acid sequence of SEQ ID NO: 2 from amino acid residue 1 (Met) or residue 23 (Lys) to residue 135 (Cys); and
   (d) a polynucleotide molecule comprising a nucleotide sequence as shown in SEQ ID NO: 7 from nucleotide 1 or nucleotide 67 to nucleotide 405.

6. An isolated polynucleotide molecule encoding a polypeptide wherein the polynucleotide molecule is selected from the group consisting of:
   (a) a polynucleotide molecule comprising a nucleotide sequence as shown in SEQ ID NO: 1 from nucleotide 1 to nucleotide 792; and
   (b) a polynucleotide molecule comprising a nucleotide sequence as shown in SEQ ID NO: 5 from nucleotide 1 to nucleotide 735.

7. An expression vector comprising the following operably linked elements:
   a transcription promoter;
   a DNA segment selected from the group consisting of:
   (a) a polynucleotide molecule comprising a first nucleotide sequence as shown in SEQ ID NO: 1 from nucleotide 161 to nucleotide 199 and a second nucleotide sequence as shown in SEQ ID NO: 1 from nucleotide 437 to nucleotide 481;
   (b) a polynucleotide molecule comprising a first nucleotide sequence as shown in SEQ ID NO: 5 from nucleotide 136 to nucleotide 174 and a second nucleotide sequence as shown in SEQ ID NO: 5 from nucleotide 412 to nucleotide 456; and
   (c) a polynucleotide molecule comprising a first nucleotide sequence that encodes a polypeptide that is the amino acid sequence of SEQ ID NO: 2 from amino acid residue 29 (Cys) to amino acid residue 121 (Cys) and a second nucleotide sequence that encodes a polypeptide that is the amino acid sequence of SEQ ID NO: 2 from amino acid residue 121 (Cys) to amino acid residue 135 (Cys); and a transcription terminator.

8. A cultured cell into which has been introduced an expression vector according to claim 7, wherein said cell expresses an insulin homolog polypeptide encoded by the DNA segment.

9. The cultured cell of claim 8, wherein the cell contains a second expression vector that has a DNA segment that encodes for a heterologous processing enzyme.

10. A method for producing an insulin homolog polypeptide comprising:

culturing a cell into which has been introduced an expression vector according to claim 7, whereby said cell expresses an insulin homolog polypeptide; and recovering the insulin homolog polypeptide.

* * * * *